United States Patent
Stadler et al.

(10) Patent No.: US 6,324,421 B1
(45) Date of Patent: Nov. 27, 2001

(54) AXIS SHIFT ANALYSIS OF ELECTROCARDIOGRAM SIGNAL PARAMETERS ESPECIALLY APPLICABLE FOR MULTIVECTOR ANALYSIS BY IMPLANTABLE MEDICAL DEVICES, AND USE OF SAME

(75) Inventors: Robert W. Stadler, Shoreview; Shannon Nelson, Stacy, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/280,203

(22) Filed: Mar. 29, 1999

(51) Int. Cl.[7] .................................................. A61B 5/04
(52) U.S. Cl. .......................... 600/509; 600/517; 600/521; 128/901
(58) Field of Search .................................. 600/509, 517, 600/521; 128/901, 923

(56) References Cited

U.S. PATENT DOCUMENTS

| | | |
|---|---|---|
| 4,546,776 | 10/1985 | Bellin et al. . |
| 4,550,370 | 10/1985 | Baker ................... 364/413 |
| 4,987,897 | 1/1991 | Funke ............... 128/419 PG |
| 5,025,786 | 6/1991 | Siegel .................... 128/642 |
| 5,135,004 | 8/1992 | Adams et al. ........... 128/896 |
| 5,199,428 | 4/1993 | Obel et al. .......... 128/419 C |
| 5,203,326 | 4/1993 | Collins ............. 128/419 PG |
| 5,313,953 | 5/1994 | Yomtov et al. ......... 128/696 |
| 5,330,507 | 7/1994 | Schwartz ................ 607/14 |
| 5,331,966 | 7/1994 | Bennett et al. ......... 128/696 |
| 5,437,285 | 8/1995 | Verrier et al. . |
| 5,458,631 | 10/1995 | Xavier ................. 607/117 |
| 5,480,412 | 1/1996 | Mouchawar et al. ..... 607/6 |
| 5,497,780 | 3/1996 | Zehender .............. 128/696 |
| 5,520,191 | 5/1996 | Karlsson et al. . |
| 5,531,768 | 7/1996 | Alferness ................. 607/6 |
| 5,535,752 | 7/1996 | Halperin et al. ....... 128/670 |
| 5,551,849 | 9/1996 | Christiansen .......... 417/472 |
| 5,752,976 | 5/1998 | Duffin et al. ........... 607/32 |

OTHER PUBLICATIONS

Jager, F. et al., "Detection of Transient ST Segment Episodes During Ambulatory ECG Monitoring", *Comput. Biomed. Res.*, pp. 305–322 (Oct. 1998) Abstract only.

Szilagyi, S.M. et al., "Comparison Between Neural–Network–Based Adaptive Filtering and Wavelet Transform for ECG Characteristic Points Detection", *IEEE*, vol. 1, pp. 272–274 (1997) Abstract only.

An Approach to Intelligent Ischaemia Monitorin (pp 749756) Medical & Biological Enginnering & Computing by A. Bosnjak.

A Compact Microporcessor–Based ECG ST–Segment Analyzer for the Operating Room IEEE Transaction on Biomedical Engineering vol. BME–29 No. 9 Sep. (pp. 642–648) by Steven J. Weisner et al.

Bedside Diagnosis of Myocardial Ischemia with ST–Segment Monitoring Technology Journal of Electrocardiology vol. 30 (pp. 156–165) by Barbara J. Drew et al.

Body Position Effects on the ECG Journal of Electrocardiology vol. 30 No. 4 Oct. 4, 1997 (pp. 285–291) by Mary G. Adams.

*Primary Examiner*—Mark Bockelman
(74) *Attorney, Agent, or Firm*—Girma Wolde-Michael

(57) ABSTRACT

We show how to determine whether there has been an axis shift in an electrocardiogram waveform and how to use this for filtering out bad electrocardiogram information and to modify an adaptive filter that can be used to adapt the filtering of such electrocardiogram information to make it available for determining physiologic conditions even after an axis shift.

18 Claims, 20 Drawing Sheets

Averaging over 2 samples to reduce AC noise

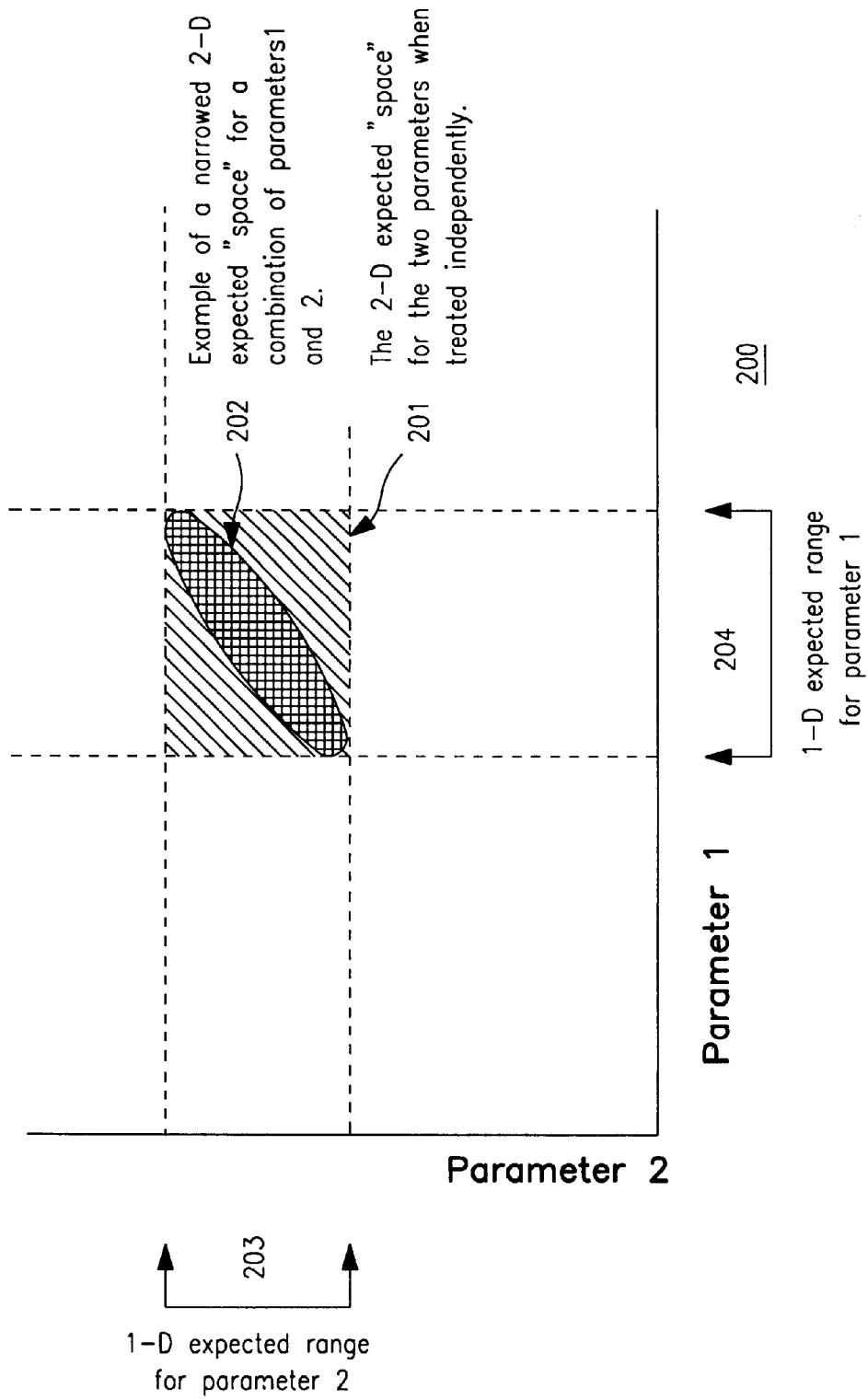

AXIS SHIFT ANALYSIS OF ELECTROCARDIOGRAM SIGNAL PARAMETERS ESPECIALLY APPLICABLE FOR MULTIVECTOR ANALYSIS BY IMPLANTABLE MEDICAL DEVICES, AND USE OF SAME

CROSS REFERENCE TO RELATED PATENT APPLICATION

Reference is hereby made to commonly assigned U.S. patent applications: Ser. No. 09/280,595 filed on Mar. 29, 1999 METHOD AND APPARATUS FOR FILTERING ELECTROCARDIOGRAM (ECG) SIGNALS TO REMOVE BAD CYCLE INFORMATION AND FOR USE OF PHYSIOLOGIC SIGNALS DETERMINED FROM SAID FILTERED ECG SIGNALS in the names of Robert W. Stadler et al., pending, Ser. No. 09/280,286 filed Mar. 29, 1999 IMPROVED METHOD FOR ISCHEMIA DETECTION AND APPARATUS FOR USING SAME in the names Robert W. Stadler et al. now U.S. Pat. No. 6,128,526, Ser. No. 09/280,592 filed Mar. 29, 1999 for DETERMINATION OF ORIENTATION OF ELECTROCARDIOGRAM SIGNAL IN IMPLANTABLE MEDICAL DEVICES in the names Robert W. Stadler et al. now U.S. Pat. No. 6,115,630.

FIELD OF THE INVENTION

This invention relates to a method and apparatus embodied in an implantable medical device (EMD) or an external medical device (EMD) for monitoring electrocardiogram signals and potentially for finding myocardial ischemia of a patient's heart and optionally applying a therapy to a patient experiencing ischemia.

BACKGROUND

Myocardial ischemia is the leading cause of morbidity and mortality in developed countries. Myocardial ischemia involves oxygen starvation of the myocardium, particularly in the bulky left ventricular wall, that can lead to myocardial infarction and/or the onset of malignant arrhythmias if the oxygen starvation is not alleviated. Although myocardial ischemia is associated with the symptom of angina pectoris, the majority of episodes of myocardial ischemia are asymptomatic or "silent."

Accurate and rapid detection of myocardial ischemia is the first essential step toward reducing morbidity and mortality from this often silent but deadly condition. Without the knowledge of the condition, it cannot be treated. A wide range of therapies are known for the treatment of myocardial ischemia once it is detected, including surgical revascularization, neural stimulation and a variety of biologically active agents or compounds which can remove blood clots, reduce cardiac workload or improve cardiac circulation.

The electrocardiogram (ECG) or electrogram (EGM) of the cardiac cycle detected across sense electrode pairs located on the patient's skin or in the patient's body, respectively, is a repetitive waveform characterized by a periodic PQRST electrical activation sequence of the upper and lower heart chambers. The PQRST sequence is associated with the sequential depolarization and contraction of the atria followed by the depolarization and contraction of the ventricles, and successive PQRST complexes are separated by a baseline or isoelectric region. The PQRST electrical activation sequence commences with the P-wave indicative of the depolarization and contraction of the atria and is followed by the QRS complex indicative of the depolarization and contraction of the ventricles. The T-wave at the termination of the ST segment time delay is associated with re-polarization of the ventricles. The PQRST electrical activation sequence with intact A-V activation detected across a sense electrode pair is fairly predictable in shape. The P-wave, R-wave and T-wave events occurring in sequence in the range of normal heart rates are usually readily recognized by visual examination of the external ECG or an EGM recorded by implanted electrodes that are correctly oriented with the depolarization waves. The P-wave and R-wave are readily sensed by sense amplifiers of a monitor or therapy delivery device coupled with appropriately placed sense electrode pairs.

The ST segment of the ECG or EGM is typically close in amplitude to the baseline or isoelectric amplitude of the signal sensed between PQRST sequences, depending on the sense electrode pair location. During episodes of myocardial ischemia, the ST segment amplitude is elevated or depressed (depending on positioning of the ECG or EGM sense electrodes in relation to the heart) from baseline. These ST segment deviations can be readily recognized by visual examination.

The physiological basis of ST segment deviation changes in the presence of cardiac ischemia may be explained by ischemic changes in the action potential of cardiac myocytes. When myocytes become ischemic, the resting potential increases (toward zero), the depolarization slope of the action potential decreases, the plateau decreases in voltage, and the duration of the action potential decreases. These changes result in voltage gradients and an "injury current" between normal and ischemic myocardium during the resting and plateau phases of the action potential. Because the voltage gradient between the normal and ischemic myocardium is positive during diastole and negative during systole, the isoelectric or baseline signal level and the ST segment signal level of the ECG are displaced in opposite directions during ischemia. The change in the isoelectric or baseline level is not easily detected because the pair of sense electrodes implanted in the patient's body are AC coupled through filters to the inputs of differential sense amplifiers. However, the disparity between the isoelectric or baseline level and the ST segment may be detected if the isoelectric or baseline point and the ST segment point can be identified.

It has long been a goal in the development of external cardiac monitors and IMDs to be able to automatically detect ST segment deviations from baseline and to accurately determine when the heart is ischemic therefrom so that the patient's cardiac condition can be assessed and treated both in the clinical setting and while the patient is outside a clinical setting. A wide number of implantable therapy delivery devices and/or monitors have been proposed for detecting ischemia and delivering a therapy and/or recording the detected ischemic events in an ambulatory patient. Fundamentally, the algorithms employed in these systems endeavor to automatically sample the amplitude of the ST segment in the PQRST complex in an EGM or ECG signal, compare its absolute amplitude against a threshold and declare an ischemic or normal condition based on the results of the comparison.

In regard to Implantable Medical Devices (IMDs), commonly assigned U.S. Pat. Nos. 5,199,428 and 5,330,507 and U.S. Pat. No. 5,203,326, are incorporated herein by reference, and describe the historical development of electrical stimulation of the carotid and vagus nerves and other nerves to relieve cardiac arrhythmias and angina pectoris associated with myocardial ischemia. Perhaps more important to the background of this invention, they also describe relatively simplistic methods for detecting cardiac ischemia. The '326 patent also proposes providing backup anti-tachyarrhythmia pacing and cardioversion/defibrillation shock therapies. U.S. Pat. Nos. 5,531,768, 5,497,780, 5,135, 004 and 5,313,953, all incorporated herein by this reference, monitor or detect myocardial ischemia and some record data related to ischemic episodes for telemetry out at a later time, to provide therapy or even to set off an alarm.

In these ischemia detection IMDs, the ischemia detection depends entirely or at least in part on the location of a fiducial point in the PQRST sequence, sampling the EGM signal level at a point within the ST segment in the PQRST sequence, and detection an elevated or depressed ST level exceeding a threshold level. Automatic detection techniques are set forth in the above-incorporated '428 and '507 patents that depend on sensing the R-wave, setting an ST segment time window timed from the detected R-wave, sampling the amplitude and/or integrating the amplitude to develop a current event ST signal level, and comparing the current event ST signal level to a threshold signal level that is derived from an average normal ST signal level. In the '953 patent, a computationally expensive template establishing and matching algorithm is set forth that determines "I" and "j" deflection points preceding and following the R-wave of each PQRST sequence as the fiducial point or points. The ST segment signal level is sampled 80 ms after the determined "j" point and is compared to the threshold signal level.

In the above-incorporated '428 patent, it was proposed that the detection of myocardial ischemia be accomplished by also sensing the patient's coronary sinus blood pH and/or oxygen saturation and comparing each to preset, normal thresholds. The sensors are located in the coronary sinus or a coronary vein to measure the dissolved oxygen and/or the lactic acid level of myocardial venous return blood. The system includes programmable thresholds against which the signals developed by the sensors and the ST segment deviation are compared. When ischemia is confirmed, the disclosed system triggered burst stimulation of selected nerves until the blood gas and/or ST segment variations returned to non-clinical risk levels. However, blood oxygen sensors that perform adequately over a period of chronic implantation have not been perfected, and blood oxygen changes can be due to conditions or physiologic states of the patient other than ischemia.

These prior approaches are also problematic for a number of reasons that contribute to the magnification of the deviation of the sampled ST signal level from the isoelectric level due to factors and conditions other than myocardial ischemia, thus registering too many false positive indications of ischemia to be very useful. Myocardial ischemia can be mistakenly detected due to ST segment changes in the PQRST complex caused by "axis shifts", electrical noise, cardiac pacing, and high sinus or tachycardia cardiac rates that distort the shape of the PQRST complex. These problems are described, for example, in "Analysis of Transient ST Segment Changes During Ambulatory Monitoring" by Franc Jager et al. at Computers in Cardiology, 1991, Los Alamitos: (*IEEE Computer Society Press* 1991; 453–456), "An Approach to Intelligent Ischemia Monitoring" by Bosniak et al. in *Med. and Bio. Eng. & Comp*, 1995, pp. 749–756, and in "A Compact, Microprocessor-Based ST-Segment Analyzer for the Operating Room" by Seven J. Weisner et al., (*IEEE Trans. on Biomedical Engineering* BME-29, No. 9:642–648.

For detection of axis shifts and eliminating their confounding effects on attempts to establish a reliable ischemia detection system, the Jager algorithm (from his article listed in the preceding paragraph) measures the electrical axis angle and the difference between the ST segment and the isoelectric level over two periods, one immediately after the other, and compares the difference in mean the parameters between these two periods to a threshold. Bosniak et al. use a multistate Kalman filter to look for step changes in ST segment, representing axis shifts. This method is far too complex for current generation implantable devices.

There remains a need for a system capable of automatically and reliably detecting ischemia. Significant advantage can be had if it is able to detect ischemia in any portion of the patient's heart. Ease of implantation, stability and long term use in ambulatory patients is obviously a consideration. Important also is that such a system reliably and consistently distinguish ischemia from other conditions or physiologic states of the patient. Additionally an indication of the location of the ischemia is useful too.

This can be characterized as a need for such a system for accurately detecting myocardial ischemia through measurements of the cardiac EGM in more than one sensing axis to account for the possible locations of ischemic regions of the heart that is easily implanted and functions reliably over time, even as the heart condition changes.

SUMMARY OF THE INVENTION

The present invention provides apparatus requirements and algorithmic processes that can be used to satisfy some or all of these needs. It contemplates a more reliable and consistent method and apparatus implementing an algorithm in an IMD which may also be useful for an external medical device for automatically and accurately detecting myocardial ischemia and triggering delivery of a therapy, data storage, and/or diagnostic assistance, as well as processing abilities to filter out bad data from electrocardiogram signals for other purposes as detailed and described within. It is also useful to find which cardiac cycles might have data which would be invalid for one purpose but which would therefore be indicative of a changing physiologic condition. Accordingly, filtering out the "bad cycle" information can yeild useful indicator data as well from the information contained in what would otherwise be considered invalid cycles.

It is thus an object of the present invention to accurately detect episodes of myocardial ischemia from sense electrodes located on the patient's skin or in the patient's body and distinguishing ST segment deviations due to ischemia from ST segment deviations that may be caused by one or more factors other than actual ischemia, including at least electrical noise, "axis shift", cardiac pacing, and distortion of the PQRST complex due to arrhythmias and high sinus heart rates.

It is a further object of the present invention to accurately detect episodes of myocardial ischemia in this manner from sense electrodes arranged to provide a plurality of sense electrode pair vectors for developing a plurality of vector ECG or EGM signals from substantially the entire heart where ischemia develops.

The collection of electrogram data includes samples taken from portions of the cardiac cycle including portions in a QRS complex, (usually to find the R-wave peak, although this is not necessary in some embodiments); and samples in the ST segment; plus at least a sample in an isoelectric area, usually prior to the QRS complex, although following the T-wave would be acceptable also for finding an isoelectric point for the processes we describe.

At least one or more of the objects are realized in a system providing, in general and preferably, at least one of the following features.

Adaptive noise detection, (i.e., the device will enable parameterizing the waveform, comparing current parameters to expected ranges, updating expected ranges from the current waveform if the majority of parameters are within range, and keeping track of the frequency with which a parameter does not fall within the expected range to adapt to abrupt rhythm changes). With these processes, an algorithm in the apparatus can adapt to accept the heart rhythm of any individual and exclude cardiac cycles that do not fit the normal pattern for such an individual. Our noise detection algorithm is free of thresholds except the number of cycles out of range that constitutes a rhythm change (this is 12 in the most preferred form of the algorithm).

An additional novel feature of the noise detection is its ability to take advantage of multiple, preferably orthogonal, vectors. In other words, rather than check if a parameter is outside of a 1-D allowed range, using our invention we can check if a vector parameter is outside of a multi-dimensional "allowed space".

Adaptation to slow changes in the rhythm of the individual by adjustments to variables we maintain in memory with values for the expected ranges of parameters, and eventual acceptance of abrupt changes in rhythm by automatic broadening of expected ranges.

We have also provided a feature designed to make the signal indifferent to AC noise (typically 50 or 60 Hz) in the ECG signals, because this is the most common frequency of noise in the modern world. In preferred embodiments we set the ECG sample rate at an integer multiple of 50 or 60 Hz and average all ECG measurements over complete cycles of 50 or 60 Hz Therefore, by sampling at twice the AC frequency, and averaging all measurements over two samples (thus producing a frequency domain "zero" at the AC frequency)we essentially eliminate the power frequency noise. This feature may have separable applicability to monitoring body signals generally.

Also, it may be noted that the ST segment measurements are conducted at multiple locations based on rate-adaptive delays from the peak of the R-wave. Therefore, at higher heart rates, the location of the ST measurement is closer to the QRS complex.

Most algorithms base ST segment location on delay from the J point. The J point is difficult to locate algorithmically. The difficulty results in variation in the actual location of measurements. Use of the peak of the R-wave temporal location for finding the places to measure the electrogram signal gives our approach an unusual starting point.

Adaptations to use the invnetion during pacing are also described.

Preferably, too, the measured ST changes are filtered so that only ST changes that occur at rates that are characteristic of human ischemia are accepted. Since commercial algorithms look at absolute ST deviation, they have trouble with ischemic ST deviations that are superimposed on slow ST drift. Commercial algorithms usually have some filter to exclude the fast "noisy" ST changes, but not to remove the slow drift. Our filters get rid of both slow and fast ST deviations. The result of our algorithm is a "relative" ST deviation as opposed to an absolute measurement of deviation. Our filters respond to ST changes at physiologic rates (measured empirically), and reject all changes outside this range as noise.

Observation of ST segment changes can take advantage of orthogonal ECG leads with our apparatus. The difference between the ST segment and the isoelectric level can be treated as a 3-dimensional vector, whose position is determined by 3 orthogonal ECG leads. (One could use our teachings for 2- and n-dimensional vectorization of the ST segment variation constraints as well). The temporal evolution of the ST vector is tracked over time for movements that are representative of ischemic changes. This improves the sensitivity of the device, and combines ECG leads so separate processing of each lead vector can be eliminated. This is similar to multidimensional noise detection described earlier in this summary, except that here the orthogonality is applied to the "signal" (i.e., the ST change), not the noise. For example, is the ST change vector moving away in space from it's expected location? At what velocity is it moving? Is this movement indicative of ischemia? If the changes are too slow or too fast they will be ignored in preferred embodiments.

Another preferred feature is the detection of axis shifts and removal of their potential confounding effects on ST segment observations. This provides an additional basis for determining good ischemia signals in ST segment analysis for ischemia, and thus good ischemia detection results. Particularly when using the other inventive analysis described herein. Axis shifts occur when postural changes (of the patient) alter the location of the heart with respect to the recording electrodes. They can cause sudden and significant changes in the ST level. We describe how to detect axis shifts by establishing expected ranges for the amplitude of the R-waves in each vector, and declaring an axis shift if the measured R-wave amplitude consistently falls outside of the expected range.

In another preferred feature, we normalize the measured ST deviations from the isoelectric point by the R-wave amplitude. Traditionally, ST deviations are measured in micro-volts (or millimeters on a standard strip chart). 100 micro-volts deviation of the ST segment is considered to be significant in the art of external (surface) ST segment deviation measurements. For an implanted device, the amplitudes of the ECG or EGM are quite different than surface ECG amplitudes. Rather than calibrate each patient's device to absolute voltage units, and derive some new significance threshold for ST changes in an implanted device, our approach has been to prefer normalization of the ST change by the R-wave amplitude makes common thresholds (i.e., 10%) applicable to all patients. (This has a multidimensional aspect as well, as the R-wave amplitude and ST deviation can be vectors, and the vector deviation of the ST segment form the isoelectric baseline can be normalized by the magnitude of the R-wave).

We also prefer to look for a positive and a negative peak after sensing that we have found an R-wave. We then compare them and choose the larger absolute valued one as the R-peak. To reduce cost or complexity, this feature may only used during setup to account for polarity switching, and then once the orientation of the R-wave is known, the first or second peak may always be chosen as the R-peak sample. It is preferrable to periodically or continually check employ this feature to be sure there is not a change in direction, however.

In another preferred feature, we provide detection of ischemia in the presence of paced ventricular rhythm. If the rhythm includes ventricular pacing the QRST morphology is distorted and standard measurements of ST segment are inaccurate for detection of ischemia. In the present invention, sporadic ventricular pacing is ignored and ST measurements are conducted (i.e., the signal is sampled) only on intrinsic beats. In the presence of consistent ventricular pacing, ischemia is detected by temporarily modifying the pacing rate (if possible) to let the ST measurements be obtained at a consistent paced rate. For example, for every minute of paced ventricular rhythm, the pacing rate would be set to 70 bpm for a period of for example, 3 beats. The ST segment and isoelectric segment measurements can them be made at these same rate paced beats. This could be done about once each minute. For the algorithm discussed within, the average R—R interval would be that of the 3 paced beat rate.

An alternative for using the other features of this invention during pacing is to use consistent pacing timing but adopt the pacing spike as the fiducial point and the times of measurement of the ST segment will then be at a constant delay from the delivery of the pacing stimulus. In other words, substitute the pacing pulse for the R-wave peak for the rest of the decisions.

BRIEF DESCRIPTION OF THE DRAWINGS

The present invention is described with reference to the following drawings, in which like parts may be denoted with like numbers, and wherein:

FIGS. 6, 7, and 9–16 are a flow chart illustrating the steps of performing the ischemia detection method of the present invention from the plurality of EGM signal data point sets.

FIG. 20 is a drawing of a three dimensional graph of multiple sensor vectors and a region definable with respect to them.

DETAILED DESCRIPTION OF THE PREFERRED EMBODIMENTS OF THE INVENTION

The process in general and device/body configurations.

Figure 6:
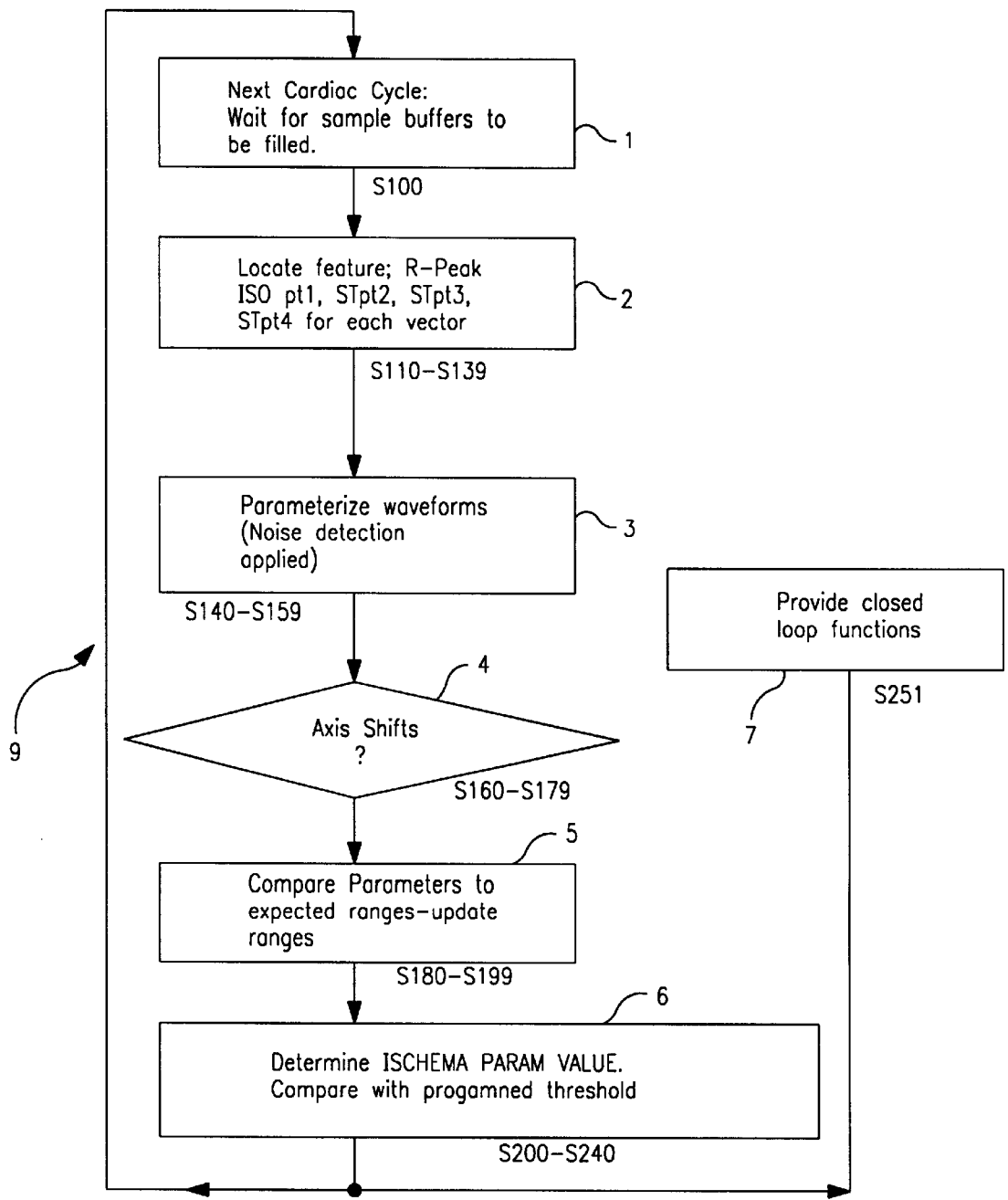
FIG. 6 is a block diagram showing a generalized set of steps employed in a preferred embodiment of invention.

The process of finding the signals that indicate the presence or absence of ischemia taught in this invention is not straightforward, but with reference to FIG. 6, the generalized process steps 1–7 of the process 9, are laid out simply. More than one set of procedures can be combined to complete all the steps laid out in FIG. 6, or they can all be done together. Thus it can be considered a plurality of inventions, since some of these processes could be used with different devices and for different purposes. Thus, one could filter out troublesome cardiac cycle signals for purposes of providing good data for other diagnostic purposes than ischemia detection, and one could employ the ischemia detection processes without some of the enhanced processing provided by excluding bad cardiac cycles, for example. Further, the use of the ischemia parameters defined by these inventive processes provides the basis for closed loop therapeutic intervention.

Referring to step 1 of FIG. 6, on each cardiac cycle, the buffers are filled with signal samples. A basic filter may be used to get rid of drift and high frequency noise. Then characteristic features of the electrocardiogram waveform are picked out in step 2. The waveform is parameterized and a complex set of noise detection steps are applied in block 3 (steps S140–S159 and similar numbers on other blocks refer to detailed process steps explained later with reference to more detailed figures). The signal values are then checked for axis shift in block 4. Then a range valuation is made to see if the parameters fit within expected ranges in block 5. At this point an ischemia parameter value can be calculated and compared with a programmed threshold in block 6. With the evaluation of this ischemia parameter, the medical device can provide what we call closed loop functions, such as neural stimulation, release of medicaments or drugs, changes in electrical stimulation of the heart, setting of alarms and so forth, and of course recording the data for diagnostic and physician usage. These are called closed loop because it means the medical device, with or without intervention by a physician or patient, can adjust to the ischemic condition, and possibly even relieve it, once it has made a determination that it exists.

Of course the preferred form of device to do this would be implantable, allowing the patient to continue with normal life activities while this closed loop activity occurs. External devices can use this invention also, however. Additionally, use of the filter parameters discussed herein will enable a medical device to find changes in cardiac rhythm that may be useful for cardioverter defibrillator response to indicated changes in patient condition.

It is generally desired that trauma be avoided as much as possible in the implantation of cardiac therapy delivery and monitoring IMDs including their associated leads and electrodes. Thus, minimally invasive procedures are employed that typically involve transvenous implantation of EGM sensing and therapy delivery leads into the patient's right heart chambers or cardiac vessels accessed from the right atrium when combined with a pacemaker or an implantable cardiodefibrillator or just whenever the right ventricular lead would be felt useful. The right ventricular electrode is typically lodged deep into the apex of the right ventricle, and a return electrode is located either on the same ventricular lead for bipolar ventricular EGM sensing or on the IMD housing for unipolar ventricular EGM sensing. The use of just a single electrode pair to derive a single EGM signal for processing to determine if ST segment deviation exists does not necessarily provide enough information to accurately detect ischemia under all conditions and locations of the ischemic area of the heart in relation to the sensing vector of the electrode pair. In some preferred embodiments we may use a number of electrodes on the surface of the IMD itself, or a number of stub or other leads that may be tunneled around the patient's body to provide an expanded set of electrode pairs from which to extract the optimum range of signals and thus have the best opportunity to detect hidden ischemic conditions.

Electrode Configurations in General

Figure 1A:
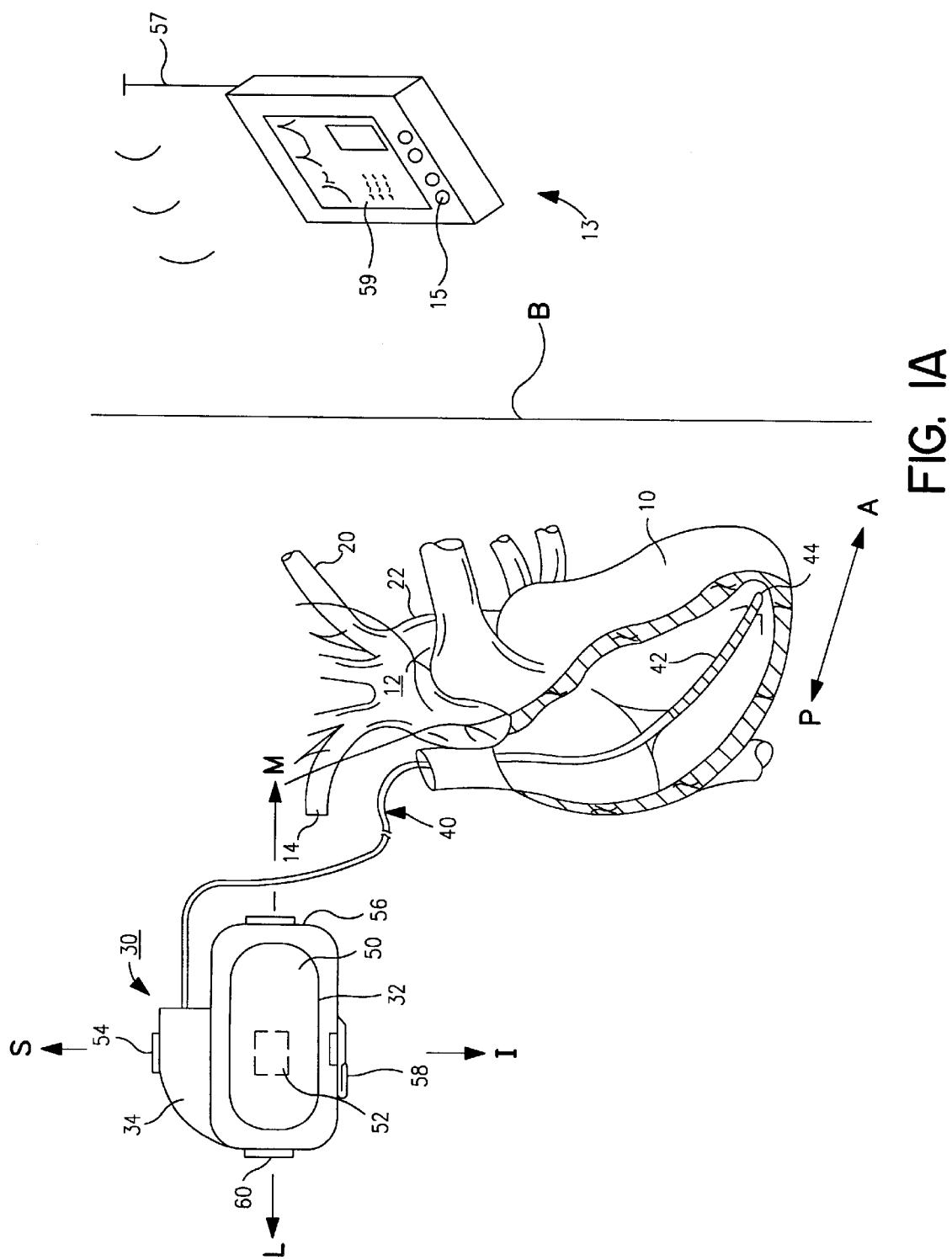
FIG. 1A is a diagrammatic illustration of the heart, its associated blood vessels and nerves, and a monitor or therapy delivery IMD of one embodiment of the present invention coupled thereto, and also illustrating an external device for communicating with the IMD.
Figure 1B:
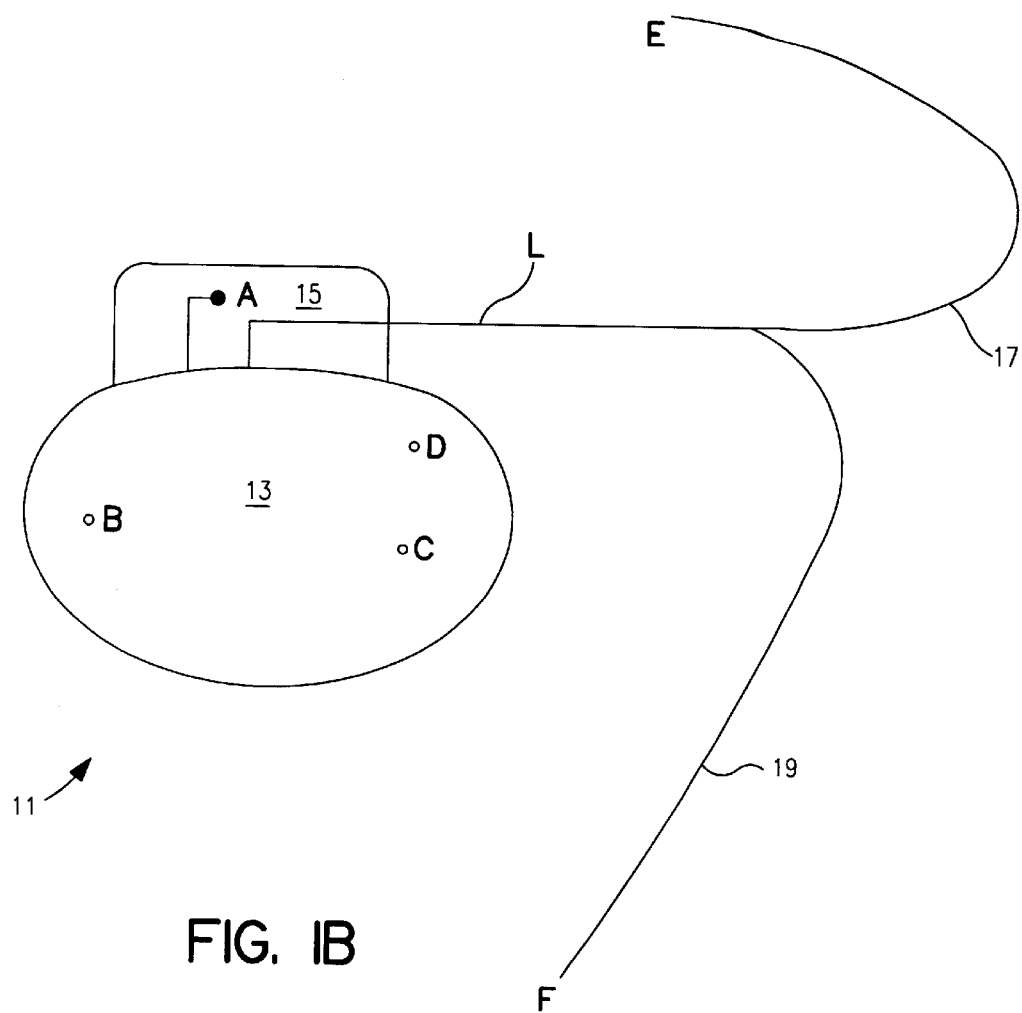
FIG. 1B is an illustration of an alternative form of an IMD for use with this invention.

In one preferable embodiment an IMD having a plurality, preferably three, EGM sense electrode pairs that are aligned as much as possible with the three axes of the body but it is not necessary that they pass through the heart, although that can provide acceptable ischemia detection resolution. Typical IMDs are shaped to have relatively flat and thin profiles so that they can be implanted subcutaneously in frontal locations of the upper thoracic regions or the lower abdominal region and remain inconspicuous. Tunneling a lead around the patient's back is a variation too. Without the electrode at the patient's back, the leads tend to provide electrode configurations yielding signals from the Coronal plane defined by the Superior-Inferior (S-I) and Lateral-Medial (L-M) body axes, although, in practice, the plane may be tilted somewhat into the Anterior-Posterior (A-P) body axis also. In FIG. 1A, the IMD sensing axes S-I and L-M are drawn through the IMD 30, and as would be apparent from relating this to common anatomical references, the A-P axis for sensing is at a right angle to both the S-I and L-M axes, extending from the front major surface to the rear major surface of the patient's body. The sense electrode pairs can take a wide variety of forms, and only one exemplary form is illustrated in FIG. 1A. Three EGM signals from the three respective electrode pairs that are preferably arranged orthogonally to the extent possible are processed in parallel in accordance with the algorithm of the present invention described below. FIG. 1B illustrates an alternative embodiment 11 with 5 electrodes A–E, three located on the surface of the can itself (B, D, and C) and one in the connector block 15 (that is, electrode A), and one for the front of the patient body or in the patient's heart, electrode E and another electrode F, for being tunneled to the patient's back, both F and E being at the far ends of lead extensions 17 and 19 from lead L.

Also illustrated in FIG. 1A, is a communications device or programmer 13, for communicating with the IMD through the patient's body B and/or the air, any data transfer that would be useful for fully utilizing the information available to the patient or physician now with the use of this ischemia detection system herein described. Thus an antenna 57 would communicate with the telemetry circuits (see FIG. 2) when required. A display 59 would enable graphic and textual interface with the physician or patient, and a series of buttons could provide for activation of commonly used or emergency type functions. A speaker/microphone (not shown) could provide for aural communications as well, such as an alarm or voice recognition.

Figure 1C:
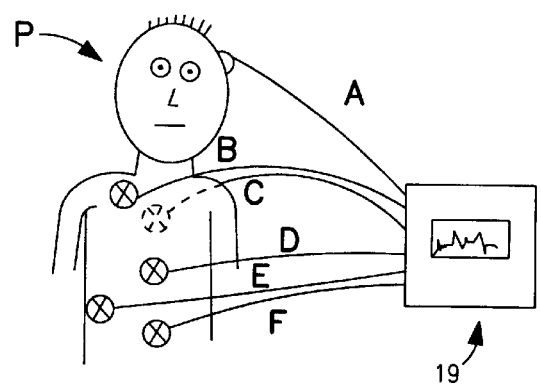
FIG. 1C is an illustration of an external system for use with this invention.

FIG. 1C provides an illustration of a patient P with a system in accord with the instant invention used implemented entirely with an external device 19, having a set of electrogram electrodes A–F positioned about the patient's body.

Figure 1D:
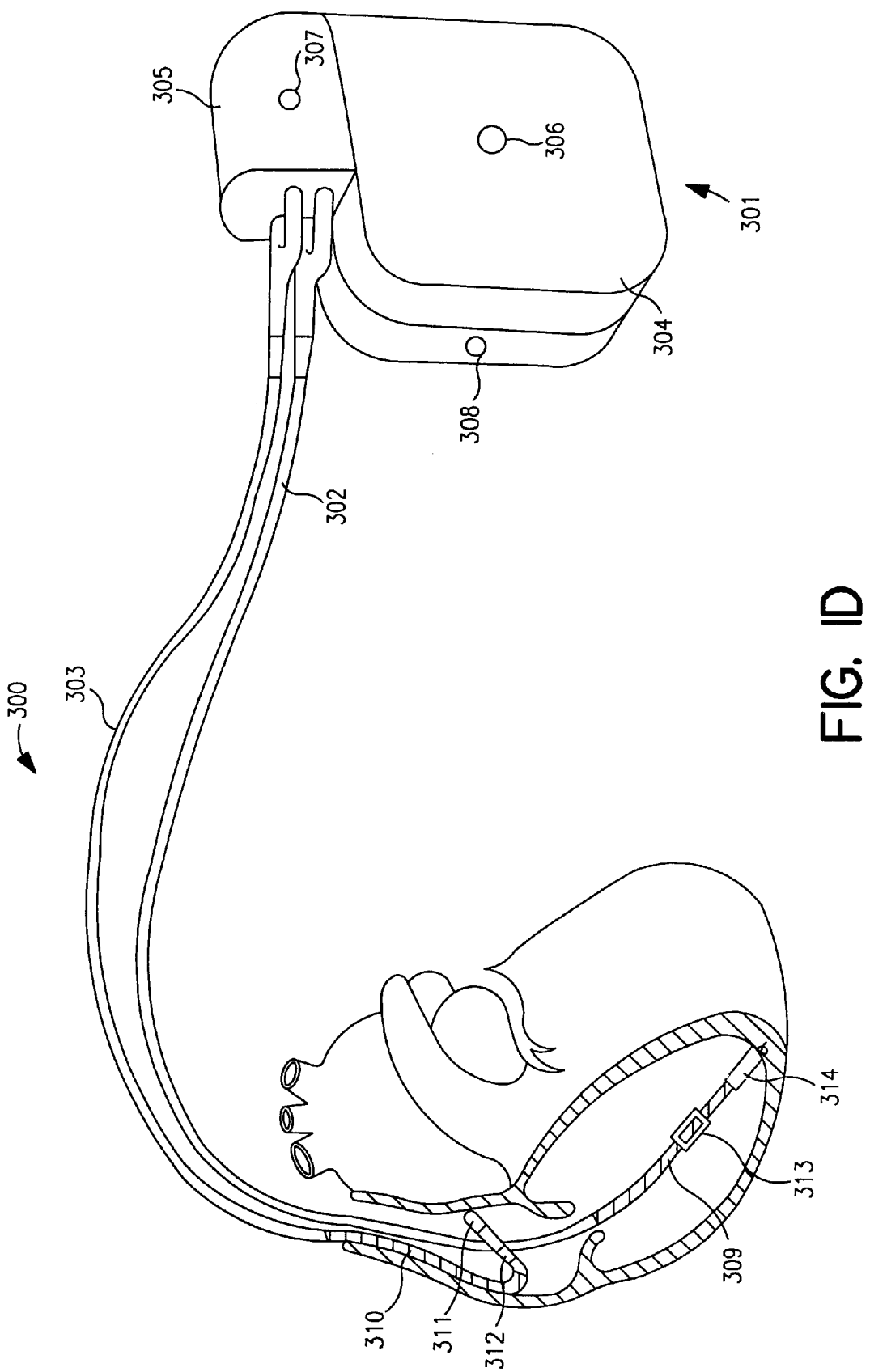
FIG. 1D is an illustration of an alternative arrangement using defibrillator electrodes and the cardiodefibrilation housing for the electrode array in accord with other preferred embodiments.

FIG. 1D prodices a sense for how the teachings of this invention may be employed in a defibrillation device. In the system 300, the cardiodefibrillator and or pacemaker 301 can employ the outer housing 304 as an electrode, and it may be additionally provided with point electrodes 306, 307,308 at various locations on the housing or the connector block 305. The typical device also has leads 302 and 303, for providing defibrillation coil electrodes 310 and 309 in two chambers. These leads may contain additional electrodes at points like 311, 312, 313, and 314, for examples. All of the lead electrodes, including the coils may be used to provide one electrode for a vector, and the best available vectors for use with this invention in such systems will most likely be between a lead elecctrode and one on the device 301.

Referring back to FIG. 1A, the IMD 30 is formed in the typical manner of a hermetically sealed housing 32 having a connector block assembly 34 attached to the housing 32 for receiving one or more proximal connector ends of one or more cardiac lead, e.g., ventricular endocardial lead 40, in this case. In this embodiment, the IMD 30 is also formed with an orthogonal Subcutaneous Electrode Array (SEA) of the type described in commonly assigned U.S. Pat. No. 5,331,966, incorporated herein by reference, or described in the above-referenced '953 patent.

The SEA electrodes comprise the four small surface area electrodes 54, 56, 58 and 60 that are mounted to the peripheral edge of the non-conductive connector block assembly 34 and the side and bottom of the housing 32 orthogonally to one another and in a planar spatial array and the two front and back electrodes 52 and 50 mounted to the planar major surfaces of the housing 32. These electrodes 50, 52, 54, 56, 58 and 60 are mounted to an insulating substrate that insulates them from one another and from the conductive housing 32. Feedthroughs (not shown) are employed through the peripheral edges and/or sides of the housing 32 to make electrical connection between the electrodes 50–60 and circuits within the housing 32 described below.

The IMD 30 is intended to be implanted subcutaneously in the patient's torso at a distance from the heart 10 such that the SEA electrodes are not in direct contact with the heart. The circuitry within IMD 30 includes three differential sense amplifiers that are selectively coupled with SEA electrode pairs in a manner to be described below such that the one-dimensional sensing axes of the three selected electrode pairs are at least physically mutually orthogonal. While the SEA electrodes 50–60 can be selected in sense electrode pairs that do have true orthogonal alignment, fewer SEA electrodes can be alternatively located about the IMD housing. Moreover, as described below, one of the electrode pairs can include a sensing electrode or electrodes located on the lead 40. In such alternative configurations, the sensing axis of at least one of the electrode pairs is angularly offset and not truly in mutual orthogonal relation with the sensing axes of the other two electrode pairs. The offset angle can be compensated for by biasing the EGM signal derived from it in a manner well known in the art.

For convenience, the sensing axes of the selected electrode pairs are referred to in the following description as the S-I, L-M and A-P sensing axes, although the IMD 30 is likely to be implanted such that they are not in true alignment with the corresponding body axes of the patient. In addition, the term "lead vector" is used herein as designating the EGM signal derived along the sensing axis of each selected pair of sense electrodes and/or the sensing axis itself. Thus, the three EGM signals are nominally designated the L-M, S-I and A-P vector signals or lead vectors as described further below.

It will also be understood from the following description that these lead vectors can be combined mathematically to derive a single or multi-dimensional "spatial vector" or a set of single or multi-dimensional spatial vectors from selected pairs of the three lead vectors. In the algorithm described below, the two or three dimensional spatial vector can be advantageously formed from the two or three lead vectors and processed as described. However, for convenience, the algorithm is described employing parallel processing of the three lead vectors with examples provided for alternatively processing spatial vectors.

It will be further understood that the algorithm can also be advantageously employed to process only a single lead vector or two lead vectors or the spatial vector derived therefrom to determine the presence or absence of ischemia. The use of all three lead vectors or spatial vectors derived therefrom provides a higher accuracy in the determination of the occurrence of an ischemic episode.

Continuing in reference to FIG. 1A, the three lead vectors generated by the three sense amplifiers are sampled and digitized in parallel to derive a plurality of ST segment sampled data point levels that are employed in an ischemia detection algorithm of the present invention for determining the onset and continuation of an ischemic episode. In one preferred programmable embodiment, one of the sense electrodes 50–60 is not used. However it is reasonable to use all six electrodes or to use 5 with one extra for redundancy, or a subset thereof to eliminate some for lack of good signal, as desirable given the circumstances which will become clear as this explanation proceeds. It is contemplated that the sets of sense electrodes that are used can be selectively programmed at implant to provide the best set of three axis EGM signals. The selection can be changed later by reprogramming to account for rotation or movement of the IMD 30 in the subcutaneous implantation pocket after implantation. Of course, the IMD 30 can be manufactured with a selected set of such sense electrodes and without the sense electrode programming capability.

To provide for the opportunity to have orthogonal sensing axes, the sense electrodes 50, 52, 54 and 58 are arranged in a nominal S-I sensing axis, and the sense electrodes 50, 52, 56 and 60 are arranged in a nominal L-M sensing axis, assuming that the IMD is implanted in the depicted orientation with respect to the patient's thoracic body axes. It must be recognized that this invention will operate with any set of electrode pairs, even if the vectors they represent are not truly orthogonal. It is simply easier to think of these vectors as orthogonal, and orthogonality is preferred, even though not required. Sense electrodes 54 and 58 are employed to define the nominal S-I sensing axis or lead vector. Sense electrodes 56 and 60 are employed to define the nominal L-M sensing axis or lead vector. The sense electrodes 50 and 52 or the elongated, large surface area (coil) right ventricular sense electrode 42 located on the lead 40 (or any electrode in that area) may be employed to define the nominal A-P sensing axis or lead vector. Any one of the unused sense electrodes can be employed as a separate ground electrode for the three EGM axis sense amplifiers and for an indifferent electrode in combination with the distal tip electrode 44 of lead 40 for unipolar sensing of the R-wave. The major surface sense electrodes 50 and 52 can be the same size or differing sizes, wherein the larger major surface sense electrode can be employed as a stimulation electrode in a pacemaker or cardioverter/defibrillator therapy delivery IMD. Thus, FIG. 1 depicts all of these possible electrodes that can be combined to form the three EGM sensing axes as described below.

The distal tip electrode 44 that is lodged into the right ventricular apex is coupled through a conductor within lead 40 to a ventricular event sense amplifier within the circuitry of the IMD 30. The ventricular sense electrode can also be connected to the electrode 42 to provide near field, bipolar sensing. The sense amplifier can be a conventional R-wave sense amplifier for detecting the R-wave in the PQRST complex and declaring a ventricular sense (VS) event (from which a fiducial point is located) as described further below.

Device Details and General Operation to Implement a Process for Finding Ischemia Optionally, the IMD 30 can also include a therapy delivery system for providing pacing, and/or cardioversion and defibrillation therapies and/or vagal or carotid nerve stimulation therapies as described in the above-incorporated '563, '428 and '507 patents. The ischemia detection algorithm of the present invention can be used to trigger or to modify a delivered therapy to alleviate or avoid exacerbating the ischemic condition or to avoid mistaken detection of a cardiac tachyarrhythmia due to distortion of the EGM being monitored and processed for tachyarrhythmia detection. For example, in a DDD or DDDR pacemaker, the upper rate limit for tracking atrial depolarizations or P-waves and providing ventricular pacing is normally programmed by the physician to a fixed upper rate, e.g., 120 bpm . If the patient suffers an ischemic episode, it would be desirable to lower that upper rate to avoid pacing the ventricles at such a rate and exacerbating the symptoms. In a tachyarrhythmia control device, anti-tachycardia pacing therapies and, optionally, cardioversion shock therapies are provided on detection of an appropriate triggering tachycardia or life threatening flutter or fibrillation.

In any of these contexts, data related to detection of ischemia is stored in memory for later uplink telemetry transmission and analysis by the physician. The IMD 30 may also include an audible alarm or a stimulation of the patient's skin to alert the patient to the detection of ischemia and/or a patient activation mechanism by which the patient can trigger storage of data into a memory circuit in the IMD, or even trigger therapy to be administered by the IMD, upon feeling angina symptoms. A real time clock can also be included in the IMD system for storage of the time and date of each stored ischemic episode, and therapy delivery data can be stored in the therapy delivery IMD context.

Figure 2:
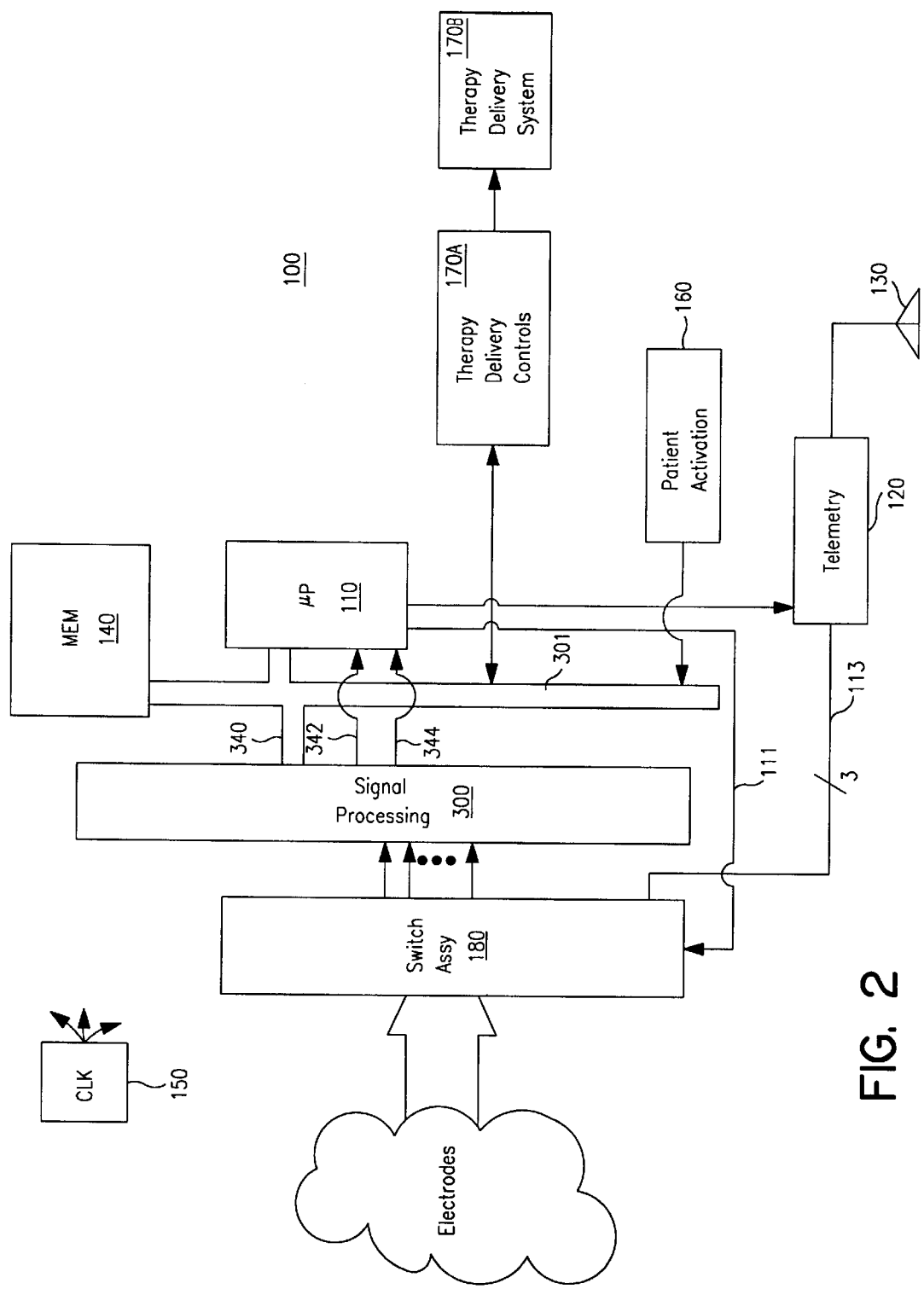
FIG. 2 is a simplified block diagram of an Implantable Medical Device (IMD) system for embodying the present invention.

Turning now to FIG. 2, the circuitry 100 of the monitor or therapy delivery IMD 30 for detecting conditions of ischemia and storing ischemic episode data in a monitoring or therapy delivery context are depicted in a simplified exemplary form. Clearly one of ordinary skill would recognize that the thicket of signal lines one would ordinarily use to communicate timing and control signals and the like among the circuit blocks shown are irrelevant to the performance of the inventive functions herein described. Likewise the use of a bus,301 to simplify communications pathways as shown may be preferred in some device builds, however they would also recognize that the memory may serve to house the buffer circuits described with reference to FIG. 3 as well as serve the microprocessor, or that it may be more efficient to build them separately. Further the system of FIG. 2 could be preferably implemented employing custom integrated circuit technology including a microprocessor 110 and associated RAM/ROM chip 140 and related circuits and data buses. Because FIG. 2 is intended to depict circuitry for a device which can provide both monitoring and therapy delivery functions through devices like those IMDs of FIGS. 1A and B, it depicts the optional therapy delivery system 170 selectively employed in the therapy delivery IMD embodiments within broken lines. An external device such as is illustrated in FIG. 1C (or an implantable device used only for monitoring) could exclude boxes 170A, 170B and possibly the patient activation box 160, if desired. A patient activation mechanism 160, which may be a switch closed by a magnetic field that the patient brings over the skin with a magnet brought to overlying the IMD 30 when the patient feels ischemia symptoms, can also be provided for initiating storage of EGM data or delivery of limited therapies.

Likewise, an external device or programmer like device 13 of FIG. 1A could be used to activate storage, transmit old stored records, cause delivery of real time multi-channel telemetry and so forth, if the telemetry circuit 120 is used to initiate such functions. The battery and power supply circuitry to all of the functional blocks, the crystal oscillator and clock circuits for timing circuit operations, and certain other functional blocks associated typically with a digital controller/timer (DCT) circuit or the microprocessor 110, as well as other features common to pacemakers, cardiodefibrillators, drug pumps and/or neural stimulators are common and are therefore not shown to simplify the illustration and focus this exposition on the invention. To illustrate here, there needs to be a therapy delivery system such as a controlling circuit 170A and a delivery circuit 170B to deliver the therapy indicated by the presence of ischemia conditions confirmed or found using this invention.

Many of the operating parameters and modes and the above-described sense electrode selections can be programmed from outside the patient's body by a programmer of the type described in commonly assigned U.S. Pat. No. 4,550,370, incorporated herein by reference. The external programmer is operated in a downlink telemetry mode wherein telemetry transmissions are effected through a telemetry antenna 130 and an RF telemetry transceiver 120. Data related to ischemia episodes that is generated in real time or is stored in RAM/ROM chip 140 can also be transmitted to the external programmer in an uplink telemetry mode using the RF telemetry transceiver 120 and antenna 130 in a manner well known in the prior art.

The basic operation of this circuitry 100 is as follows. The electrodes selected by select line 111 under microprocessor control determine the configuration of the switch assembly 180. This passes the signals to the signal processing circuit 300, which can convert them to digital values for storage in buffers, which may be in memory circuit 140. Indications of R wave peak timing and the presence of an R wave detection may be forwarded to the microprocessor circuit directly on lines 342 or 344, or be retrieved from locations in memory depending on how the system is configured. The microprocessor circuit under program control will follow the procedures for manipulating the data values stored in the buffers as described in detail starting with FIG. 6.

Likewise under program control, the microprocessor 110 will direct signals to the therapy delivery control circuit(s) 170A as indications of ischemia are required by the programs for the particular therapy control circuit 170A it is addressing.

Further, patient activation may cause the storage of buffered data or portions thereof under program control executed by the microprocessor. Either patient activation or an external programming device such as device 13 of FIG. 1A can send signals through telemetry antenna 130 and circuitry 120, to accomplish these patient activation functions and other functions alluded to earlier in this discussion. If desired the microprocessor will activate the direct telemetry of a representation of the analog EGM signals across lines 113, which in the preferred embodiment will be three EGM signal lines for three channels, as the signal transpires.

Figure 3:
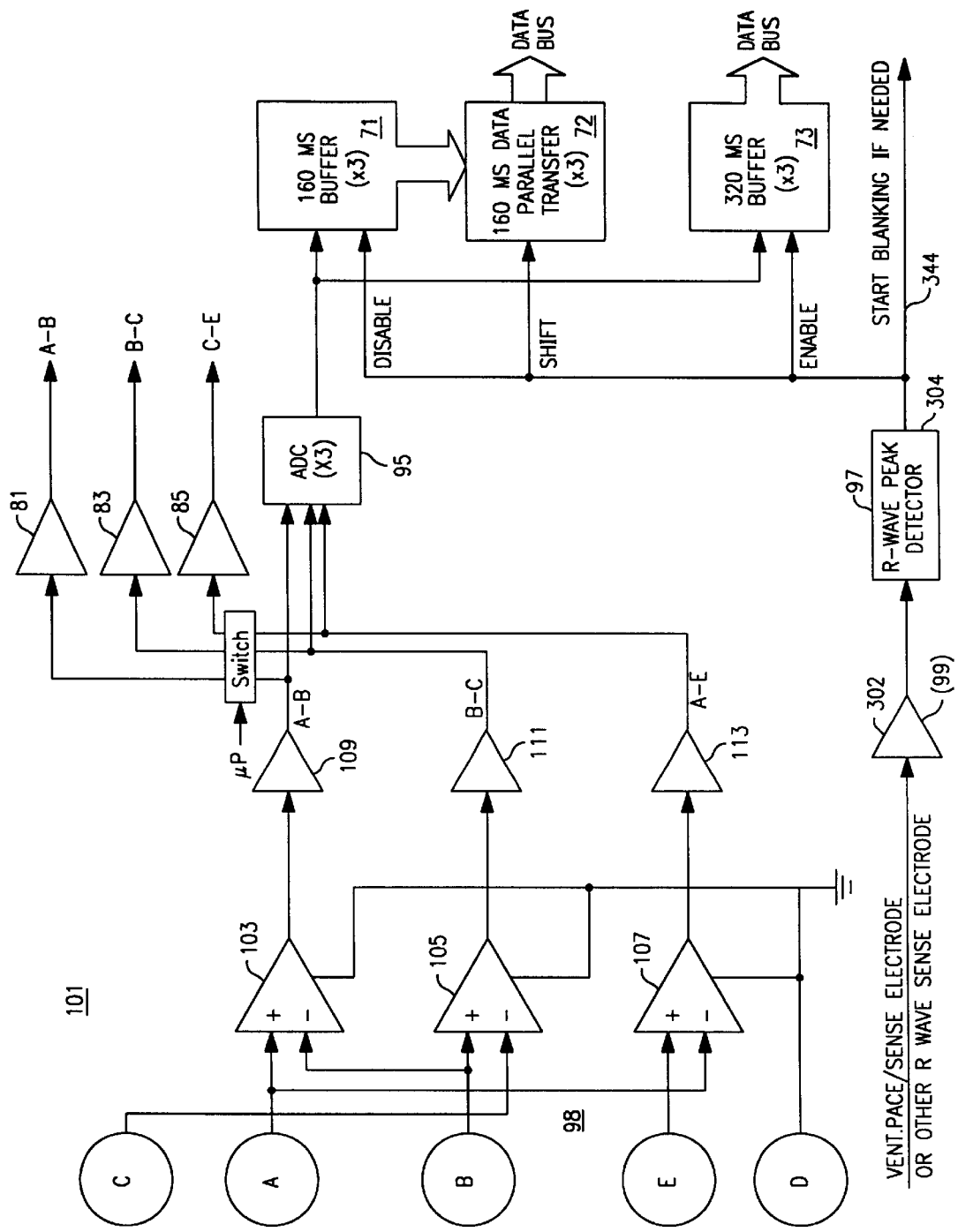
FIG. 3 is a circuit block diagram illustrating the implementation of several features and parts of preferred embodiments.

The ST segment signal processor 300 is depicted in greater detail in FIG. 3, selectively coupled at its input terminals to electrodes which may be selected by the microprocessor, here connecting electrodes "A",–"E" to three differential amplifiers 103, 105, and 107 so as to produce the vector signals A-B, B-C, and C-E at the output of amplifier stages 109, 111, and 113. The electrode D is operating as a body ground to let the variation in background signal in the body be somewhat washed out, by connecting it to the ground input of the three differential amplifiers 103, 105, and 107. Another way to describe the value of Electrode D in this context as a body ground is for rejection of common mode signals by the three differential amplifiers. Thus in the orientation described from these electrodes in FIG. 1B, amplifier 113 produces an electrocardiogram vector between the connector block electrode A and the one potentially mounted into the back of the body E, or in the A-P plane. Electrodes B-C and A-B are in the coronal plane providing rough correspondences with the plane formed by the axes SI and LM. As stated before other configurations are allowed.

The microprocessor can allow these analog electrocardiogram waveform signals to be sent directly to telemetry through the SWITCH circuit. controlled by the microprocessor, preferably or directly by an outside signal from the patient activation circuit, so that analog tracings can be viewed instantaneously outside the patient's body. The output of these amplifiers 81, 83, and 85 would thus be sent to the telemetry circuit 120 of FIG. 2.

The signals are also, of course, sent to the Analog to Digital Circuit ADC 95 so they can be converted to digital values and fill the two triple buffers (one for each vector) 71. With a shift buffer 72 included, the output of the 160 millisecond buffers 71 and the 320 millisecond (after the R-wave) buffers 73 can be output onto the data bus together, but the hardware designer of ordinary skill in this area may provide for alternative arrangements to output the sampled and digitized output signal values than is shown here. Also shown is the means by which the output of the ADC can be diverted between the buffers 71 and 73, here the R-Wave peak detector.

It must be recognized that these could be electrodes A–E from FIG. 1B, or any other set of input electrodes for the purposes of this invention. The important thing is that a set of vectors, that is more than one, are available, each of which corresponds to some orthogonal vector in the anatomical structure of the patient being looked after. In this illustrative example we use 3 electrodes and 3 pairs for inputs to the input amplifiers, but one could adopt 3 electrodes to two input amps or 5 to 4 amps, and so forth if desired, with a corresponding decrease or increase in the number of available vectors for processing. Also the selective combinations can be made through programming the programmable switch assembly 180 or can be permanently made at the time of manufacture of the IMD 30.

However they are selected, the ST signal processor 300 provides the orthogonal EGM signals or lead vectors labeled A-B, B-C, A-E, to indicate they represent the signal across these inputs from corresponding electrodes in the patient's body, be they SEA or lead tip (or ring-type or defibrillator type) electrodes. They can be sent out for real time reading to an external device by sending them to the telemetry transceiver 120 for uplink transmission in real time in response to a command received via a downlink telemetered interrogation command if desired. Or they can simply be used by the IMD itself.

The ST signal processor 300 samples and digitizes the orthogonal EGM signals S-I, L-M, and A-P at a certain sample rate (example rates include 60 to 256 Hz, and should be selected mainly based on the resolution desired and the available processing power; in the preferred examples we use 120 Hz). The processor 300 temporarily stores the sample values. The ST signal processor also processes the sensed R-wave derived by the ventricular sense amplifier coupled to a selected sense electrode pair 44 and 42 or 58, for examples, and derives an R—R interval that is provided to the microprocessor on line 342. The sensed R-wave is also used to trigger storage and transfer of a number of sample values of the orthogonal S-I, L-M, and A-P lead vectors preceding and following the sensed R-wave to the microprocessor 110 via data bus 340. The microprocessor 110 processes the plurality of EGM signals pursuant to the algorithm described below to derive an ST parameter signal that is compared to a programmable ST segment threshold to declare the existence of ischemia if it exceeds the ST segment threshold and deliver a therapy and/or store data related to the ischemia episode. It will be understood that there may be one to three ST parameter signals derived from the three EGM signal vectors that are compared to a single ST segment or ischemia parameter thresholds stored in memory or to three such dedicated ischemia parameter thresholds. The ST segment signal processor 300 preferred process for deriving the ST parameter signals is set forth in the flow charts commencing with FIG. 6.

It should be noted that the R-wave peak detector can be as described in detail herein or one could use other reliable methods for determining the R—R interval or the start of an R-wave. It is important that some determination be made so that processing can begin on the buffered data, thus the appearance of an R-wave is linked to a particular data sample as will be described in detail below.

Figure 4:
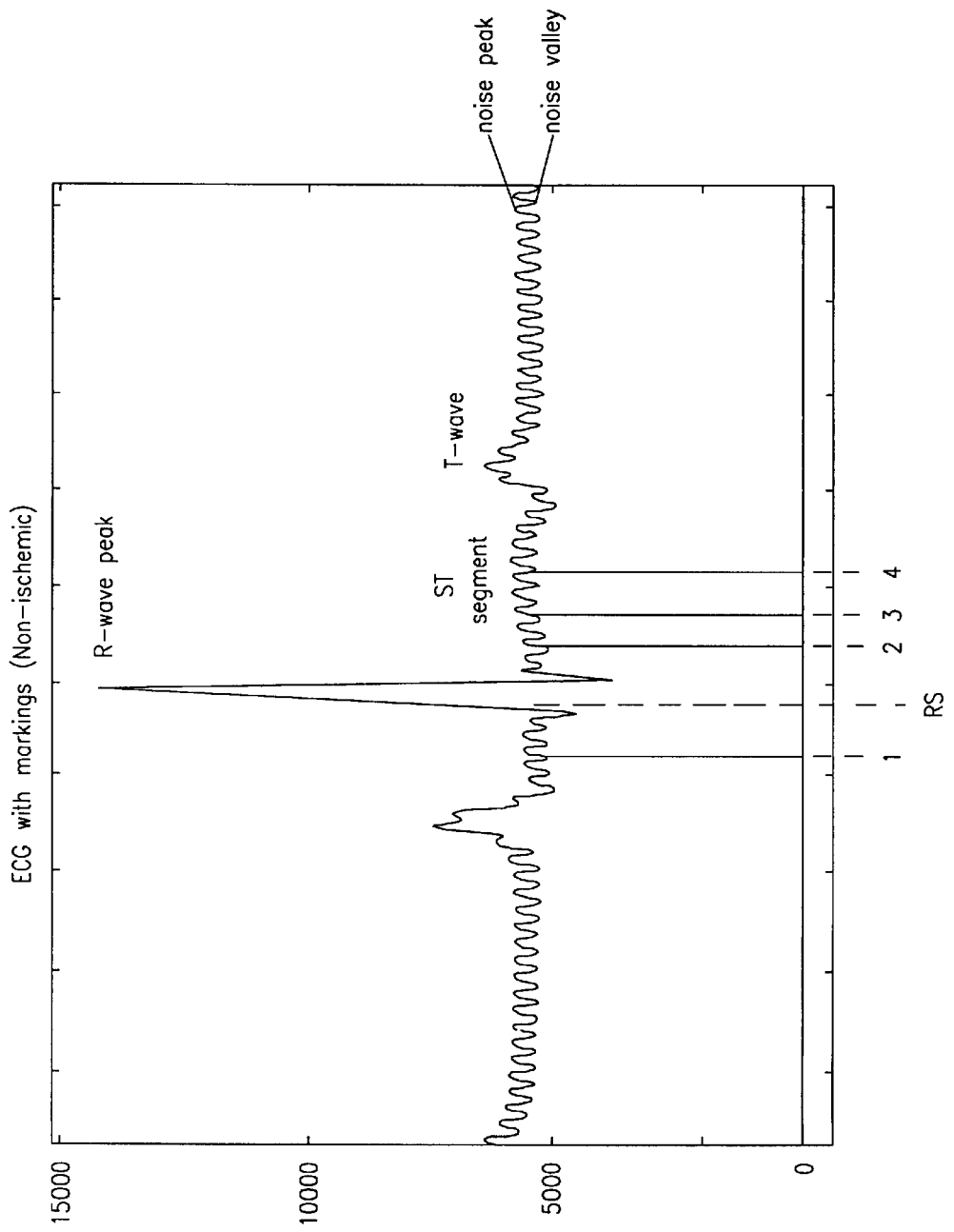
FIG. 4 is a graph of an EGM waveform of an exemplary cardiac cycle illustrating a non-ischemic ST segment deviation and sample points employed in the ST segment processing algorithm of a preferred embodiment of the invention.
Figure 5:
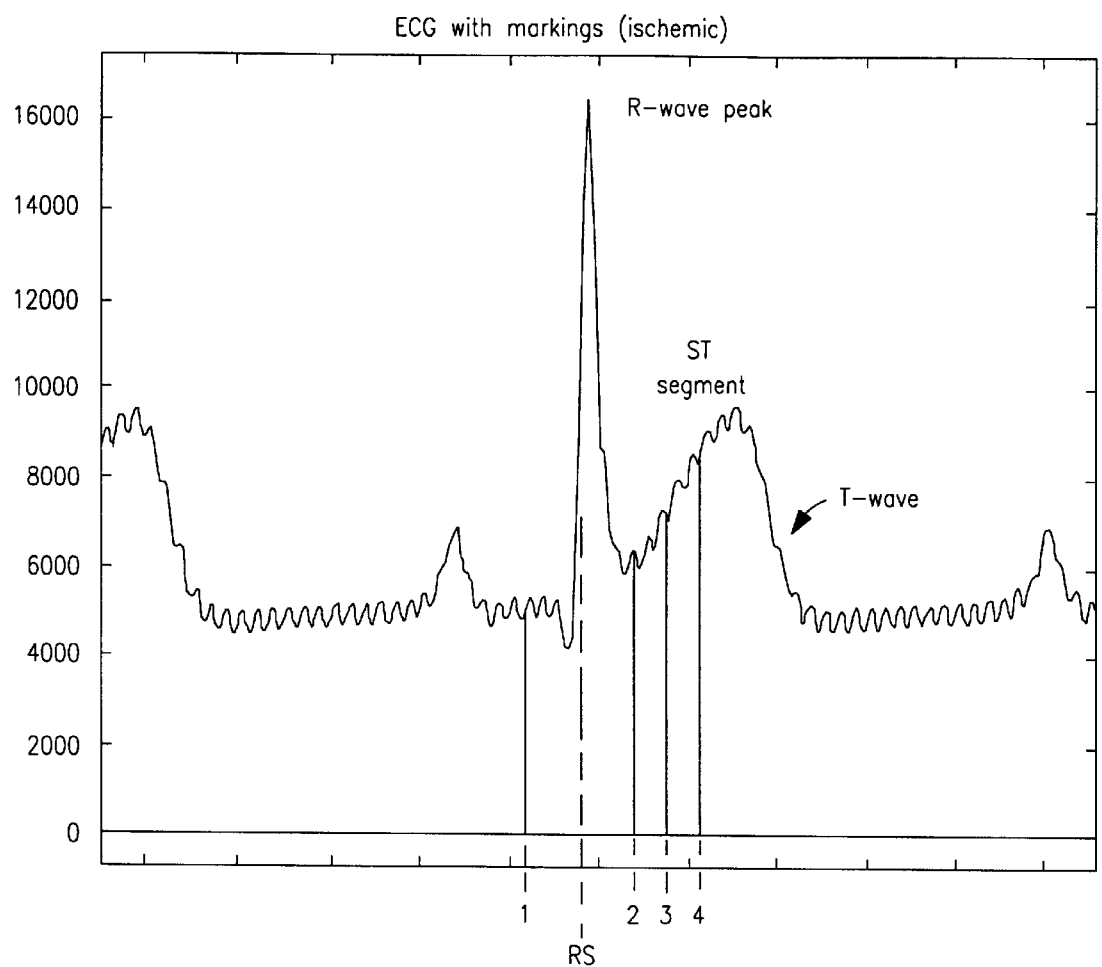
FIG. 5 is a graph of an EGM waveform of an exemplary cardiac cycle illustrating an ischemic ST segment deviation and sample points employed in the ST segment processing algorithm of a preferred embodiment of the invention.

The measurement of the ST segment deviation along each sensing axis involves defining a set of sampled time points in a measurement window timed from the detection of the R-wave or the R-wave peak. FIGS. 4 and 5 are EGM waveforms of exemplary PQRST complexes during cardiac cycles illustrating non-ischemic and ischemic ST segment deviation, respectively. Sample points 1, 2, 3 and 4 are employed in the ST segment processing algorithm of a preferred embodiment of the invention. Myocardial ischemia results in multiple changes in the EGM waveform data sets designated for each vector. We prefer to have orthogonal vectors and may designate them as S-I, L-M and A-P vectors assumed to be derived from between three different selected electrode pairs. These changes in the EGM signals caused by myocardial ischemia may include ST segment elevation or depression, changes in R-wave amplitude, T-wave inversion, increase in Q-T dispersion, and alternans, which is characterized by different PQRST morphology of alternate PQRST complexes. The changes in the ST segment deviation and polarity are the easiest to detect, are the most recognized and accepted signs of ischemia by physicians, and are likely to be the most sensitive and specific signs of ischemia that can be derived automatically from the EGM using an algorithm.

In the non-ischemic EGM waveform of FIG. 4, the disparity between the isoelectric or baseline level as sampled at point 1 preceding the VS event and any of the sample points 2, 3 and 4 during the ST segment between the fall of the R-wave and the termination of the T-wave is slight. By contrast, the disparity between the isoelectric or baseline level sampled at point 1 and any of the sample points 2, 3 and 4 during the ST segment illustrated in FIG. 5 is great and can be readily detected by thresholding techniques.

However, it is necessary to consistently locate the isoelectric periods and the ST segment with confidence despite variation in the heart rate that shortens and lengthens the ST segment and other conditions that distort the ST segment amplitude, shape and length including electrical noise signals that are superimposed on the EGM waveform and vary the instantaneous ST segment amplitude and axis shifts, cardiac pacing, etc. For example, low amplitude 50 Hz or 60 Hz electrical noise is shown superimposed on the EGM waveforms of FIGS. 4 and 5. This noise can be filtered out during the sample point value measurement in a manner described further below, or as desired. It is certainly preferable to remove the cyclic noise.

The detection of the R-wave starts the process of determining the fiducial point in the cardiac cycle from which the sample points for sampling the signal amplitude in the isoelectric region and during the ST segment are accurately timed. The most readily recognizable and detected fiducial point of each cardiac cycle is the positive or negative R-wave peak or R-peak which exceeds the preceding P-wave by a substantial margin when the R-wave sense electrodes are located in or on the ventricles. (One could use the timing from the kind of R-wave detectors used in pacemakers more typically, but we prefer what appears to be a more certain point in the R-wave cycle so we adopt this method of finding and using the R-peak point). The R-wave can be detected between any two electrodes, for example, lead tip electrode 44 and lead electrode 42 or one of the unused SEA electrodes 50–60 using a simple bandpass/derivative filter followed by a slew rate threshold detector that operates similar to a conventional R-wave sense amplifier that is also blanked for a time period after detection. Such an R-wave sense amplifier 302 that generates a VS event signal and is then blanked in this manner is included in the ST signal processor 300 depicted in FIG. 3. In accordance with one aspect of the preferred ST segment processing algorithm of the present invention, sampled data points of the sensed EGM signals S-I, L-M. and A-P (or A-B, B-C, and C-E) which have been collected into the buffers are used for processing when the VS event is detected, preferably by the sense amplifier 99. The data points closest to the actual R-peak of each of the sensed EGM signal sets are determined, and the sample points 1, 2, 3, and 4 (from FIGS. 4 and/or 5) are captured relying on the fiducial point; the peak of the R-wave; in our preferred embodiment.

The amplitudes of the orthogonal EGM signals or lead vectors S-I (A-B), L-M (B-C) and A-P (C-E) may be sampled at an 8 ms sample rate (120 Hz sampling frequency) and digitized in parallel in the ADC block 95 to continuously generate data points that are entered into three parallel 160 ms buffers in block 71 on a FIFO basis. The digitized sample points of each of the orthogonal EGM signals may also be applied directly to RF telemetry transceiver 120 for real time uplink telemetry transmission when that operation is enabled as described above.

The VS event signal is generated on line 344 when the R-wave sense amplifier 302 detects an R-wave, and the R-wave sense amplifier 302 is then blanked for a set blanking period to avoid double sensing of the same R-wave. The current R—R interval (i.e., the heart rate) may be determined from the previous VS event by an R—R interval calculator in R-wave peak detector 97 or which operation could be performed by microprocessor 110 in response to the successive VS event interrupts. In a pacemaker or cardiodefibrillator other circuits may provide R-wave or VS detection signals as well. The VS event signal is applied to disable inputs of each of the three 160 ms buffers in block 71 to disable them from receiving further data points on bus 340 from the ADC. The buffer contents, comprising all the digitized sample points of each signal S-I, L-M and A-P prior to the VS event, are passed through parallel transfer logic block 72 to the microprocessor 110 via data bus 340. At the same time, three parallel 320 ms buffers in block 73 are enabled to receive the next 40 data points (when sampled at 120 Hz, about 80 if at 256 Hz) sampled from the three EGM signals until they are filled. When they are filled, the contents of the three parallel 320 ms buffers in block 73 are transferred on data bus 340 to microprocessor 110.

It should of course be recognized that the vectors for sampling the electrocardiogram signals may be determined by a physician, or set up in accord with a testing program or simply be set as a default.

The microprocessor 110 temporarily stores the transferred data points in RAM in RAM/ROM chip or memory 140 for determination of the sample point closest to the R-peak, the isoelectric data point 1 and the three ST segment points 2, 3 and 4 of FIGS. 4 and 5 in relation to the R-peak sample point and for further processing. The 60 data points that are transferred on data bus 340 representing each EGM signal or lead vector S-I, L-M, and A-P are preferably processed in parallel.

The General Algorithm

FIG. 6 sets forth a high level block diagram of the main steps or stages of performing the ischemia detection method of the present invention that is preferably implemented by a program in memory, used by the microprocessor 110. In step 1, or Step S100 simply the standby function is performed between VS events that involves the continuous sampling of the signal levels of each selected input electrode pair, and temporary storage in the buffers. As described above, when the VS event is recognized, a group of samples are stored from before the event, and a larger group of serially obtained samples are stored after that. Preferably, at least 16 samples (128 ms) are taken before the VS event (the suprathreshold sample) and 40 samples (320 ms) after the VS event of the PQRST complex of that cardiac cycle; and these samples are stored in the three parallel buffers (one for each vector or lead), to be subsequently passed via data bus 340 to the microprocessor 110. Thus we can mark the sample coincident in time with the VS event and have collected another 30–50 samples at the preferable rate of 120 Hz, after the VS event.

Figure 7:
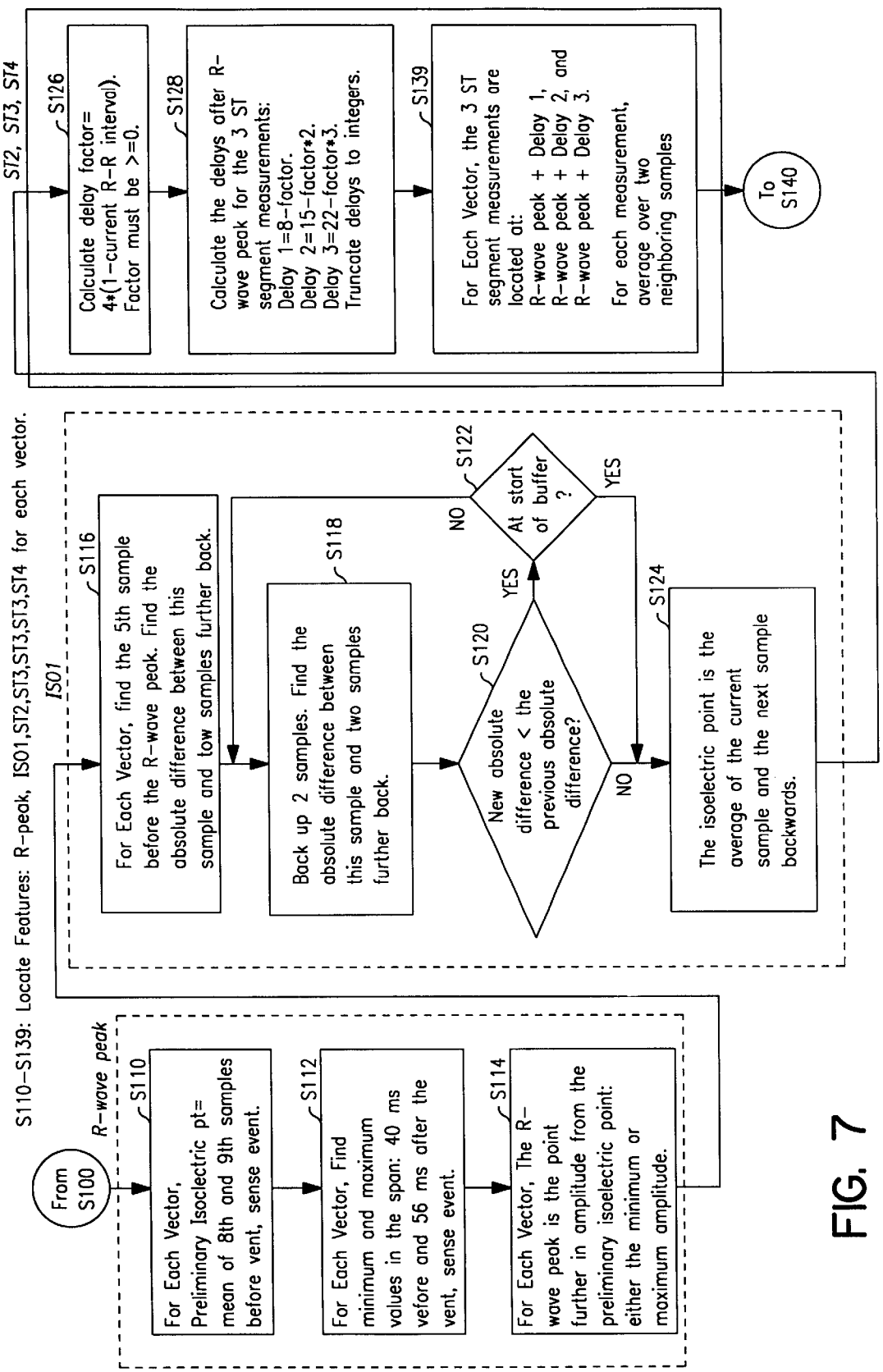

The second stage, step 2, of FIG. 6 comprises steps S110–S139, shown in FIG. 7, wherein data values for each of the R-peak, the isoelectric point 1, and the ST segment points 2, 3 and 4 are identified, thus locating the features of primary importance to us in the waveforms such as those illustrated in FIGS. 4 and 5. This can be done under program control by the microprocessor using memory in the buffers themselves or in a separate memory as desirable.

In step 3, the data is "parameterized." That is, the features of the segment of ECG waveform are characterized. The R—R interval is taken, the R-wave slope figured, a value determined for the noise in the isoelectric segment, the slope of the ST segment found a parameter called ST Change is found and the R-wave peak amplitude is found, all in steps S140 to S159, described in more detail below with reference to FIGS. 9–11.

In step 4, a determination must be made as to whether there has been an axis shift in the vectorized ECG waveforms. This process is described with reference to FIG. 12, steps 160–179.

Figure 13:
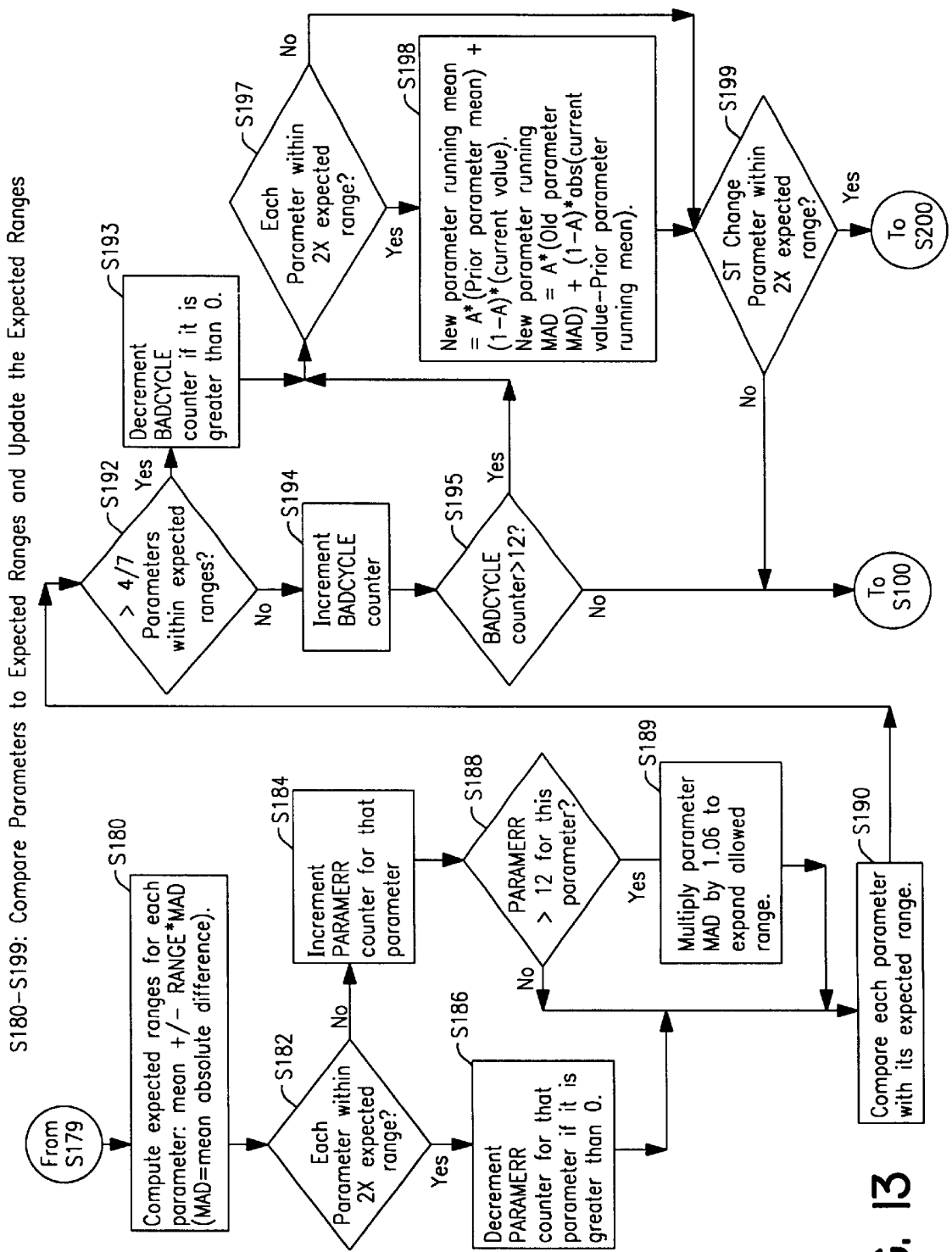

In step 5, steps S180–S199 of FIG. 13 are used to describe how the parameters are compared to their expected ranges and how the ranges are maintained.

Following step 5, in step 6, the ST Change signal values are filtered in a complex process in order to evaluate the ischemic condition of these vectorized ECG inputs. This takes numerous inputs from the already performed functions in the preceding steps and processes them in steps S200 to S240, explained with reference to FIGS. 14–16.

With the now evaluated ischemia value, the system can perform additional monitoring, therapy and alarm functions in step S251, or simply continue collecting samples as in step S100 and following the steps already outlined.

It is noted that the steps 1–3 and 5 of FIG. 6, provide a separately useful process for any physiologic signal to be determined using an electrocardiogram, such as T wave variation, ischemic condition or QT variation, which could be used to detect actual or incipient arrhythmias for example.

Also, the axis shift determination by itself may be used to avoid using bad data from determination of such physiologic indicators in the electrogram signal.

Further, the determination of an ST change signal value for each (good) cardiac cycle and filtering it to determine an ischemia parameter value can be done on unfiltered cardiac signals, cardiac electrogram signals filtered in a different manner or taken without axis shift determination, and accordingly it is believed to have separate utility.

Finally, the closed loop functions have their own obvious utility, treating ischemia, which can much more reliably be determined by resort to the other independent features of this invention.

The Details of the Algorithmic Processing

In the steps illustrated in FIG. 7 and in other steps of the algorithm, data point values are preferably averaged over at least two samples (taken 8 ms apart) in order to obtain an average value over a complete cycle of 60 or 50 Hz noise. The average value would then be used for the data point. If a complete set of data points is operated upon, this averaging can be done at any stage in the process as should be recognized by anyone of ordinary skill in the data manipulation arts.

Figure 8A:
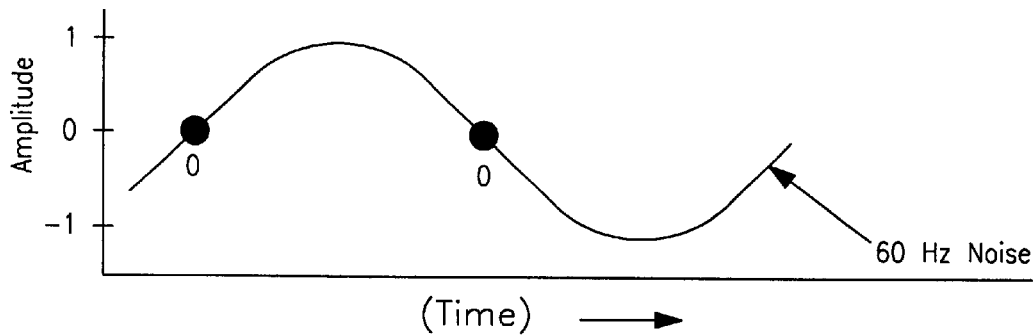
FIGS. 8A–C are diagrams of a 60 Hz noise waveform.
Figure 8B:
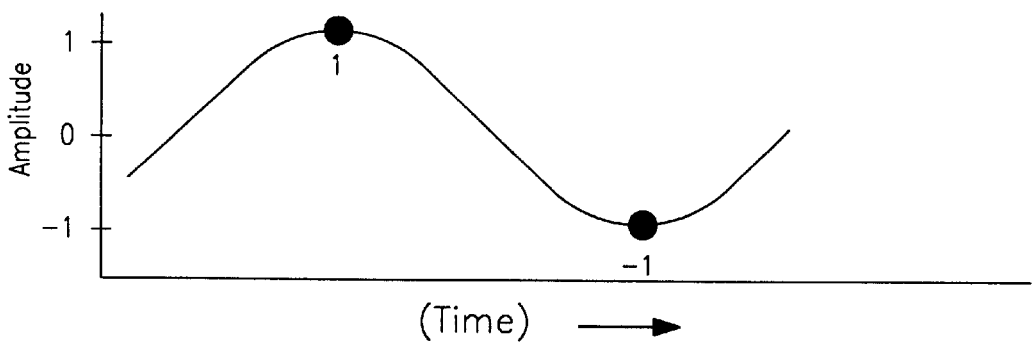
Figure 8C:
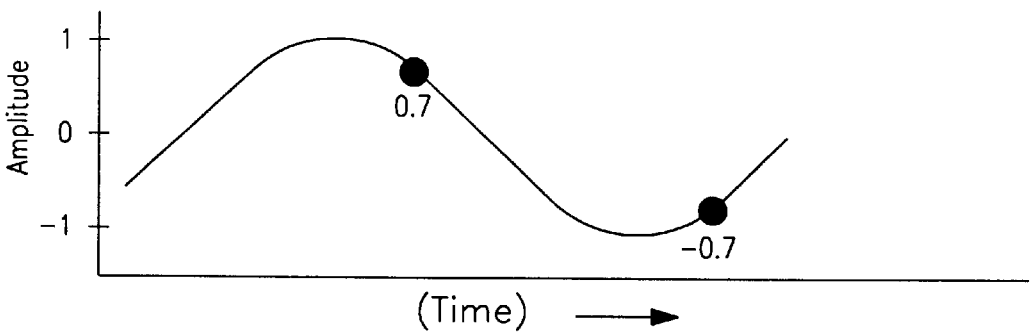

FIGS. 8A–8C illustrate this noise filtering technique in three cases where the successive sample points fall in different phases of a 60 Hz noise signal cycle. The algorithm is made indifferent to 60 Hz AC noise through the use of this technique.

Referring now to FIG. 7, steps S110–S114 illustrate the process of locating the data point values closest to the actual R-peak within the buffered samples that were preferably taken substantially as described with reference to FIGS. 2 and 3. The R-peak value may be either a positive or a negative value, depending upon the orientations at which the vectors were collected and sampled, relative to the depolarization wave originating from the heart. In step S110, a preliminary isoelectric point is selected as the average values of the $8^{th}$ and $9^{th}$ sampled data point values that were stored in the buffers prior to the VS event interrupt. (Recall that the VS event interrupt may be based on a determination of a ventricular depolarization wave occurring though any method/apparatus for determining a VS event known in the art and using it to generate a signal. The samples 8 and 9 are prior to the VS event in the buffer).

Then, in step S112, the minimum and maximum data point values are found in the samples taken about the time of the R-wave indicator signal, the VS event interrupt. They will be the largest and smallest (or greatest positive and greatest negative) sample values in the portion of the electrocardiogram collected in the case of a relatively normal cardiac cycle. In the preferred embodiment these are the sampled signal values taken within the 5 samples (40 ms) before the VS event and 7 samples (56 ms) after the VS event. In Step S114, the program compares the differences between the minimum value in these sampled values and the preliminary isoelectric point data value and the maximum value in these sampled values and the preliminary isoelectric point data value. The difference that is larger indicates the orientation of the vector from which it is taken and the value of that difference which is larger is the assumed height of the R-wave for that vector. That highest point (in absolute value) also then gives us the important fiducial point for the peak of the R-wave within the collected portion of the electrocardiogram. With the R-peak data point determined for each vector of buffered data points, it is used to determine the data points 1, 2, 3 and 4 indicated on the ECG wave forms, examples of which are illustrated in FIGS. 4 and 5. (This is done independently for each vector). Beginning at 5 samples (40 ms) before the R-peak sample, the algorithm marches backwards in steps of two samples, searching for a local minimum in the absolute slope between successive samples as illustrated in steps S116–S124. (It will be understood by a programmer of ordinary skill how to make a program sort through samples to produce this algorithm. Detailing the setting up of a sort routine, comparisons et cetera is considered well outside the range of needed disclosure since these processes are translatable into software which can operate the microprocessor to accomplish these algorithmic steps, and will be necessarily different for every processor). A slope is measured as the absolute difference between two samples that are spaced apart by two samples. The two sample spacing is to avoid measuring the slopes introduced by 50 Hz or 60 Hz AC noise which would otherwise corrupt this search with this common noise frequency, but is unnecessary if the noise is controlled for otherwise. The search concludes when a local minimum of slope is found, or when the search reaches the beginning of the stored data points of the PQRST complex. The isoelectric point 1 value is then averaged over 2 samples (16 ms). In FIG. 7, this procedure is described with reference to steps S116–S124, as an algorithmic do loop.

In Steps S126–S139, the ST segment measurements are conducted at three locations in the collected and buffered electrogram portion indicated by delays D1, D2 and D3 timed from and following the R-peak. The delays D1, D2 and D3 for ST segment data point value measurements are normally set at about 90 ms (or about 11 sampled data points), 135 ms (or about 17 sampled data points), and 180 ms (or about 22 sampled data points). In step S139, the three ST segment data point values are therefore normally selected at R-peak +90 ms, R-peak +135 ms, and R-peak +180 ms. Delays D1, D2 and D3 are converted into data point buffer locations for the full 480 ms buffer contents in step S139. The two successive data points in the buffers that are closest in time to each such adaptive delay are averaged in step S139 to derive the actual sampled ST segment value.

However, the three delays D1, D2 and D3 depend on the current R—R interval and are therefore adjusted in steps S126 and S128 to be proportional or adaptive to the current heart rate. For example, at faster heart rates, the ST segment is closer to the R-peak; therefore, the three delays D1, D2 and D3 are shortened proportionally (in an inverse manner) with the change in rate. In step S126, we use a preferred delay factor calculated as equal to 4 times (1 second minus the current R—R interval). If however the heart rate is less than 60 bpm, thus making the R—R interval larger than 100 ms, the delay calculation step will still report zero as output. For example, the delay factor is 2.0 when the R—R interval is 500 msec and the heart rate is 120 bpm. In step S128, the delay factor is used in the depicted equations to adjust the delays D1, D2 and D3. For example, if the heart rate is 80 bpm, the R—R interval is 750 ms, and the delay factor is 1 calculated in step S128. The delays D1, D2 and D3 are expressed in numbers of 8 ms sample points. Therefore the rate adjusted sampling points are subtracted from the numbers 8, 15 and 22 in step S128, yielding sample points of 7, 13 and 19 (times 8 ms, the sampling period) from the peak of the R-wave, corresponding to 56 ms, 104 ms, and 152 ms, respectively, from the R-wave peak, to the right if you are reviewing FIGS. 4 and 5. These delays will then provide pointers to the sample values at the preferred locations for points 2,3, and 4.

Figure 9:
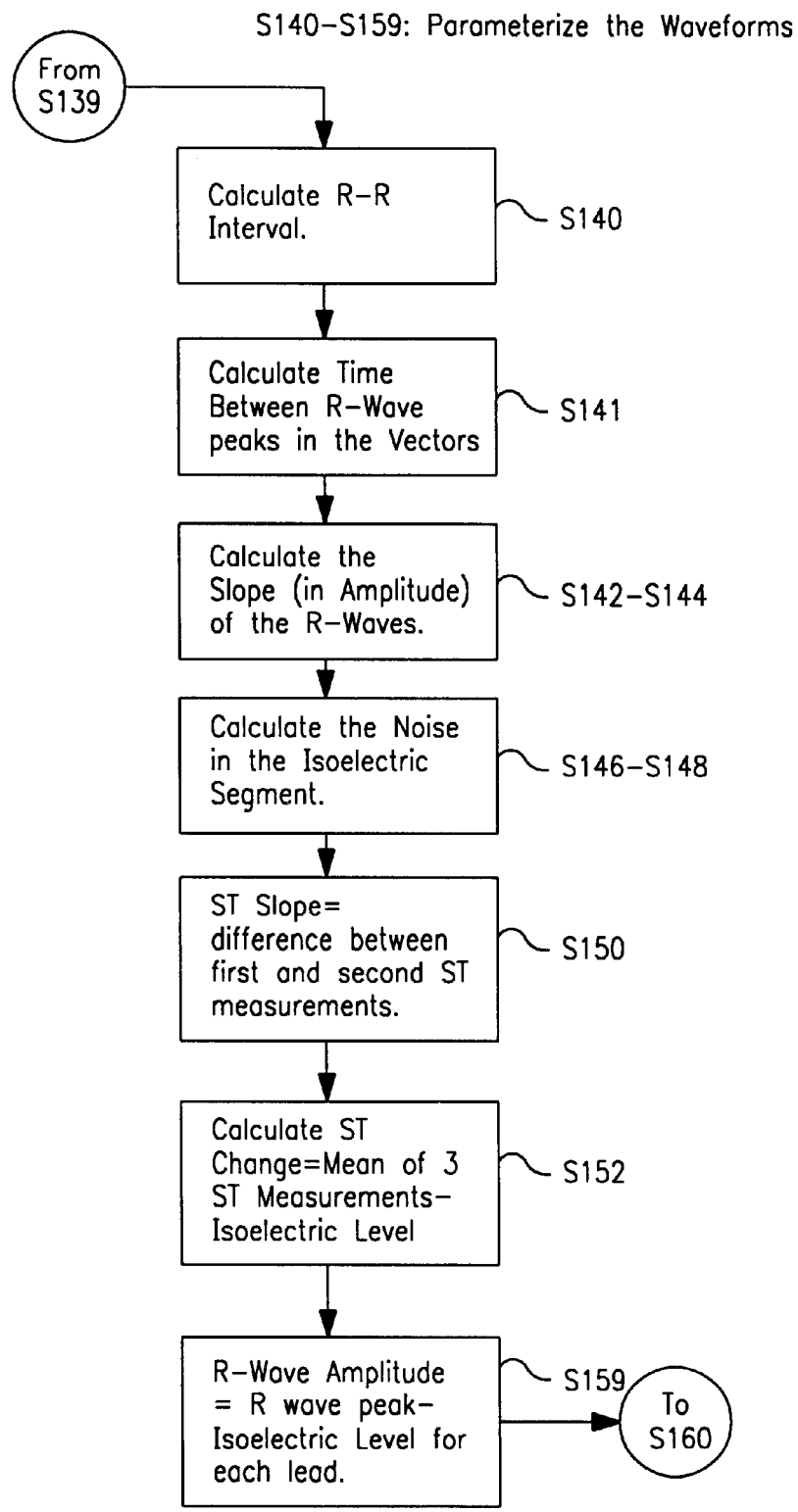
Figure 10:
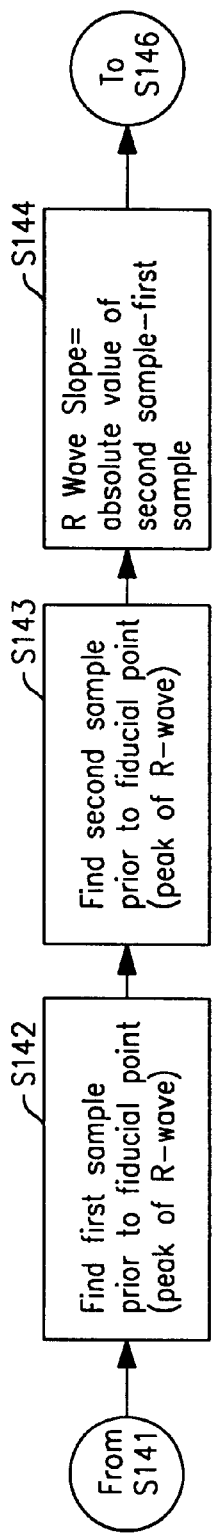
Figure 11:
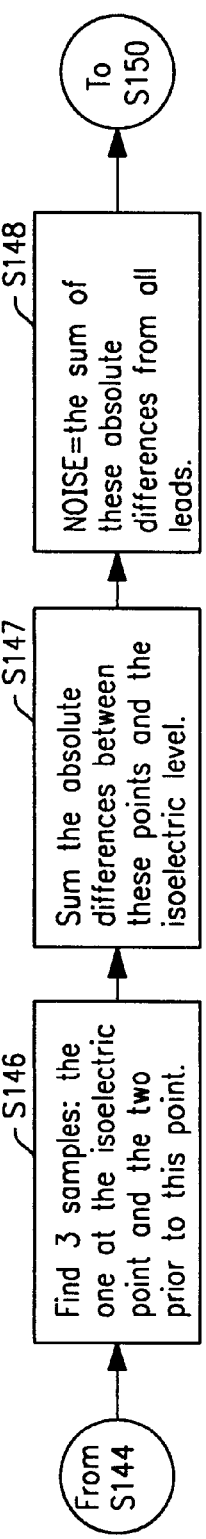

Before referring to FIG. 9, please consider where we are in relation to FIG. 6. In the third stage (steps S140–S159) of FIG. 6, seven different waveform parameters are derived as shown in FIGS. 9–11 to characterize the PQRST waveforms. Some of them may be derived from each of the vectors and some are derived from a combination of vectors, represented by the sampled data point sets for each of the three electrode pair vectors. The programmer of ordinary skill can easily build an algorithm to process the buffered data representing the sampled signal values to produce the parameterization described in the following description. The seven waveform parameters which are made from the buffered data are as follows.

1. The R—R interval parameter (step S140), which can be kept for each vector or the same one used for all further calculations as desired.

2. The R-peak jitter parameter, i.e., the variation in relative timing of the R-peak data points in the three lead vectors (step S141). If there are 3 vectors, three values are determined, if 2 only one, if 4, 6 values are preferably determined and stored.

3. The R-wave slope parameter of the three R-waves of the three lead vector PQRST complexes (steps S142–S144) is taken for each vector 4. The combined NOISE parameter representing noise in the isoelectric segment (steps S146–S148). This can be done for each vector or averaged and only one value used. We prefer using only one value 5. The ST segment slope parameter of the three ST segment measurements (2,3, and 4) of the three lead vector PQRST complexes (step S150). There preferably should be a value found for each of the vectors for this parameter.

6. The ST segment change parameter (step S152). There should be one for each vector.

7.) The R-peak amplitude parameter of the three R-waves of the three lead vector PQRST complexes (step S159). There should be one of these for each vector.

These parameter values are then used in the axis shift determining stage (steps S160–S179) and the parameter checking stage (steps S180–S199). If no axis shift is detected and if the current parameters satisfy the parameter checks, then the ischemia parameters are determined and compared to the programmed ST parameter thresholds in the final stage (steps S200–S240) before being recorded in memory for later use, used for altering therapy, and so forth.

In step S140 (FIG. 9), the R—R interval data may be retrieved from an R—R interval calculator specifically subtracting time elapsed values from R peak to R-peak, or keeping a log and reporting out the value of elapsed times. Or, the value of the R—R interval may be derived from another process in the implantable device, borrowing the data from interval timers that already exist in pacemakers, cardiodefibrillators and the like. This value (from whichever source is preferred) is stored for the R—R interval parameter for this R-wave's set of buffered data.

Recall that in step S114 of FIG. 7, the three R-peak values were calculated for the data points for the three lead vectors. The relative timing of the R-peak data points in the three lead vectors is determined in step S141 of FIG. 9 to determine an R-peak jitter parameter. High amplitude noise will likely cause disparities in R-peak detection timing in the three lead vectors. (The timing of the R-peaks in our preferred embodiment must be within the expected range (discussed below with respect to FIG. 13) to be accepted.)

Then in step S142–S144 shown in detail in FIG. 10, the R-wave slope parameters of the three R-waves of the three lead vector PQRST complexes are calculated. In each case, the first and second sampled data point levels prior to the R-peak data point value are located in steps S142 and S143. In each case, the absolute value of the difference between the first and second sampled data point levels prior to the R-peak data point value is determined in step S144. The actual R-peak data point value is not used because it is not known if this data point value is on the rising or falling edge of the R-wave. Thus, the slope figured for R is the absolute value of the first point minus the second point.

The noise in the isoelectric segment is calculated in steps S146–S148 as the sum of the absolute differences between the isoelectric data point value (which, preferably, is an average of 2 samples, itself) and preferably three sample data point values including the two points used to find the isoelectric data point value. The three data point values are located in step S146.

In step S147, the absolute differences from the three data points and the ISO1 point value found in step S146 for each lead vector are summed together. In step S148, the sums arrived at in step S147 are summed together to derive a combined NOISE parameter value for the current PQRST complex. (One could easily average them too, but as long as the processing is consistent from each cardiac cycle's portion of data, there is no need for the extra processing step averaging the vector's noise values would entail). This value NOISE can then be used to determine if the samples collected for this cardiac cycle are acceptable from a noise standpoint or should be discarded. This noisy signal rejection could be done here or the noise value stored for later processing.

Three ST segment slope parameters are calculated in step S150 as the absolute value difference between the first and second ST segment data point values taken for each lead vector. The ST segment change parameter for each lead vector is calculated in step S152 as the difference between the mean of the three ST data point values and the isoelectric data point value. The R-peak amplitude parameters are calculated as the difference between the value taken at the R-wave peak data point and the isoelectric data point of each of the three lead vectors in step S159.

The combined single parameter values derived in steps S140, S141 and S146–148 and the individual parameter values for each lead vector derived in steps S142–S144, S150, S152, and S159 are preferably retained in registers for use in the following steps of the algorithm until they are replaced when the next PQRST complex is processed in the steps S100–S139 described above.

Dealing with Axis Shifts

Rapid changes in the electrical axis of the heart can cause rapid changes in the ST segment which are not associated with ischemia (see Adams et al., *J. Electrocard.* 1997; 30:285, and Drew et al., *J. Electrocard.* 1997; 30(suppl): 157). Such axis shifts are most often caused by a change in posture. For example, an axis shift can cause an immediate deviation of the ST segment that can mistakenly be classified as representing onset of ischemia if the sampled ST segment value is compared to and exceeds an ST segment threshold.

In the present invention, as described in detail with reference to FIG. 12, axis shifts are tracked and compensated for automatically. The seven parameters derived in steps S140–S159 and processed in steps S180–S199 will be used to determine if a satisfactory number are within defined narrow "expected" range and all are within an expanded range. In steps S160–S179, if an axis shift is detected, its detection causes a type of "reset" of the algorithm. In this reset process, expected ranges of all of the ST segment parameters determined in steps S140–S159, except the R—R interval parameter, are instantly broadened. This allows the expected ranges to adapt to the new steady-state parameter values that occur in an axis shift, thus allowing for the retention and use of valuable data samples in the presence of axis shifts while avoiding false positive ischemia detection.

Figure 12:
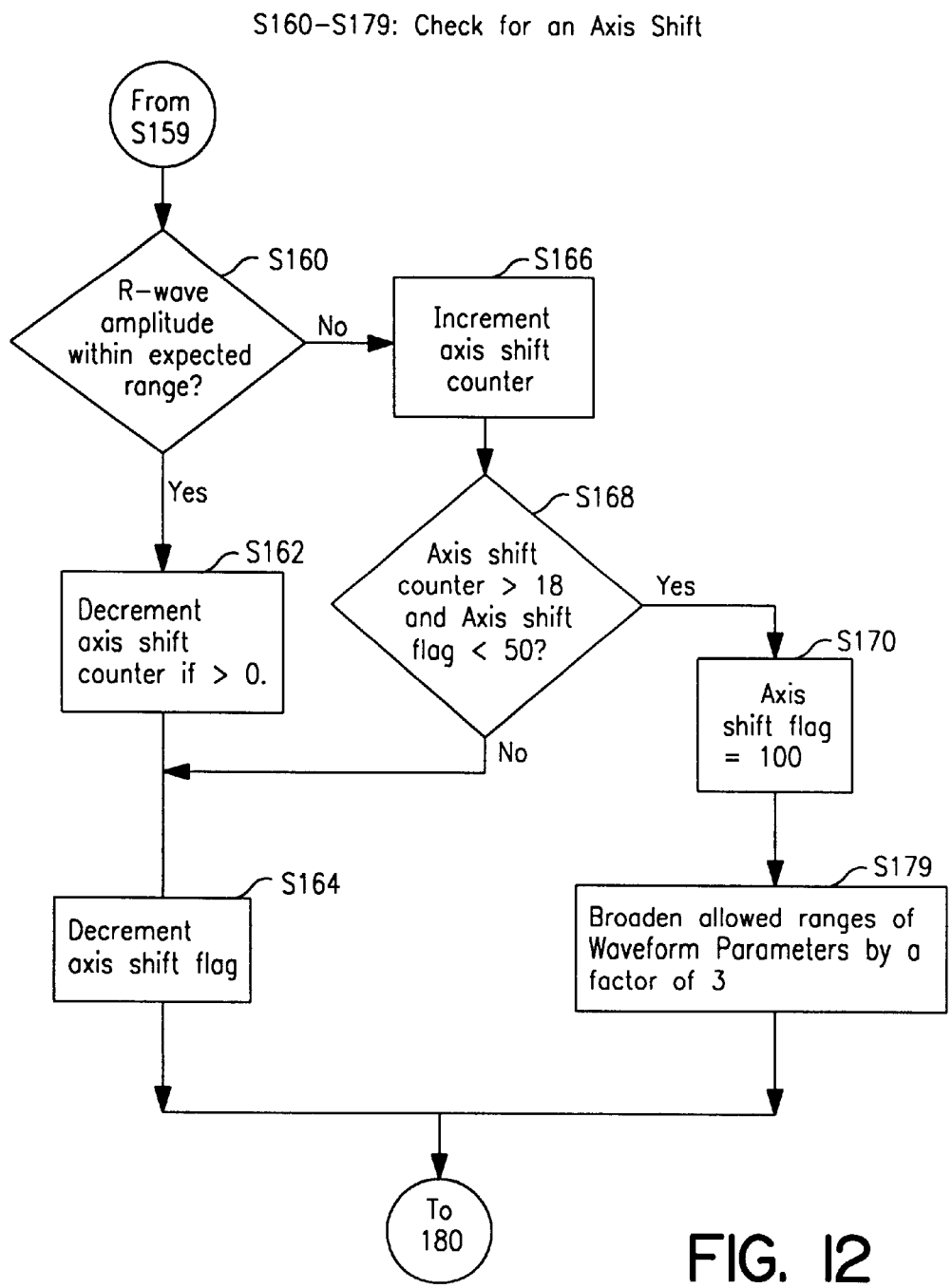

FIG. 12 shows the preferred implementation of the axis shift handling steps. The R-wave amplitudes are first compared to their expected ranges in step S160. If the R-waves are within the expected range, the count of an Axis Shift counter is decremented, as long as it is greater than zero, in step S162, and the count of the Axis Shift Flag counter is also decremented, and then the R-wave axis shift procedure waits for the next set of data from the next cardiac cycle. If the R-wave amplitude is out of range, the Axis Shift counter is incremented in step S166. The count of the Axis Shift counter is compared to 18 and the count of the Axis Shift Flag counter is compared to 50 in step S168, keeping the relevant number in an appropriate range. If these conditions are not met, then the count of the Axis Shift Flag counter is decremented in step S164 and the procedure is again finished for this round.

If an axis shift is declared in step S168, and the allowed ranges of the seven waveform parameters are broadened by a factor of three in step S179 when the count of the axis shift counter exceeds 18 and the count of the Axis Shift Flag counter is less than 50. In addition, the count of the Axis Shift Flag counter is set to 100 in step S170 in order to limit multiple axis shift detections from a single axis shift event. The count of the Axis Shift Flag counter is subsequently decremented by 1 each cardiac cycle in step S164.

Thus a kind of filter is established which generates an axis shift response signal (broadening the ranges) if there is a jump out of range for long enough to cancel the occasional short term indicator of a shift that is noise, but not allowing for a rapid series of axis shifts to make the expanded range meaninglessly broad.

The steps in FIG. 13 determine if we will use the data from a given cardiac cycle for determining ischemia. They also permit the acceptable ranges for the parameters to be adjusted. In FIG. 13, the seven waveform parameters for noise detection (defined in the steps S140–S159) are compared to adaptive "expected" expected ranges at two different levels ("near" and "far"). The system preferably maintains values for a mean and mean absolute difference (MAD, like a standard deviation but easier to calculate) of the paremeters in a memory location or register set, and determines if the current parameter lies within the MAD of the mean to the positive and negative side of the mean, that is, within an expected range. Clearly other ways could be used to set the expected range for the parameter, but this seems preferred for implantable devices. In one preferred form, to find the expected range, the MAD is multiplied by a constant, thus the expected range is the mean +/−range*MAD. In the block diagram of FIG. 13, the "far" expected range is exactly twice as large as the "near" expected range. The extent that the waveform parameters are out of range affects how the current cardiac cycle is used to update the expected ranges. If more than 2 of the 7 parameters are out of the "near" expected range, the current cardiac cycle is not used to update any of the expected ranges or to detect ischemia. Additionally, any individual parameter that is outside the "far" expected range is not updated by the current cardiac cycle. For example, if the ST Change parameter is within the "near" expected range of the running mean +/−2×(running mean absolute difference [MAD]), the ST Change parameter is not considered "noisy". If the ST Change parameter is between the running mean +/−2×MAD and the running mean +/−4×MAD, then the ST change parameter is "noisy" but the current value is still used to update the mean and the MAD. If the ST Change parameter is outside of the running mean +/−4×MAD, then the ST Change parameter and all of the filters that are used to estimate the ischemia parameter are not updated by the current cardiac cycle.

If individual parameters consistently fall outside of the "far" expected range, e.g., for 12/12, 13/14, 14/16, etc. beats, then the algorithm considers the parameter to have made a step transition to a new state (i.e., a sudden change in rhythm). In this case, the allowed range is forced to expand exponentially (by multiplying the value of the current MAD by 1.06 every beat) until the parameter is back into the "far" expected range. After re-establishing the parameter, the allowed range will slowly shrink to fit the current rhythm. In this way, the algorithm adapts to accept any rhythm from any patient, but is able to reject transient episodes of arrhythmia or noise corruption.

A block diagram of the parameter comparison and expected range updating process of steps S180–S199 is presented in FIG. 13. Beginning at step S180, the expected ranges for each parameter within each vector, if relevant for that parameter, is calculated based on the last MAD and the new parameter value from the current sampled waveform. Then the process in step S182 determines if each current parameter value is within two times the value of the expected range, if they are, S186 a PARAMERR counter is decremented for that parameter down to zero where it would stay if it gets that low. If however the parameter being checked is not within 2× its expected range, the PARAMERR counter for that parameter will be incremented in S184. If the result of incrementing this PARAMERR counter is that this has been incremented often enough that there is a clear change, manifest as an abrupt change in value for that parameter (here we use a counter value of 12 as the preferred level). Then step S188 will start the process of modifying the MAD to let the range for this parameter to expand toward the change in step S189. In all events (captured by using three counters in the preferred embodiment, a decremented, an incremented but not up to 12, and an incremented over 12 PARAMERR counter for this parameter) the process is repeated for each parameter, until all the parameters are reviewed.

It should be clear that parameters from multiple vectors are first combined to result in 7 parameters, total. That is, 3 R-Wave slopes combine such that the R-wave slope is in the expected range only if all 3 of the R-wave slopes are within their respective expected ranges. Or, in some preferred embodiments, if the combined vector parameter for the R-wave slope is within its expected "space" then the R-wave slope parameter is within its expected range. (Refer to FIG. 20 for explanation of expected space).

At step S190, all the parameters are compared with their expected ranges to determine whether we have a bad cardiac cycle of information. At steps 192, if more than a sufficient number of them, we prefer a majority of them (here >4/7 is preferred) are within the expected ranges, we decrement a BADCYCLE counter (again until it reaches zero). If the reverse is true, we increment the BADCYCLE counter. When the BADCYCLE counter is incremented, the current cardiac cycle is excluded from the process of updating expected ranges and from the calculation of the ischemia parameter. However, if the incrementing and decrementing leaves us with a counter value greater than 12 (our preferred threshold value, but a close number may be all right too), we suspect that an abrupt change in cardiac rhythm has occurred, and the expected ranges must be allowed to adapt to the new steady state. Therefore, these "bad" cycles are included in the process of updating the expected ranges and in the calculation of the ischemia parameter. Finally, an additional criteria is imposed before the current value of a parameter is allowed to be included in the process of updating its expected range: The current value must be within twice the expected range (step 197). This is a simple way to exclude outlier points from the adaptive process, while including enough points outside the expected range to keep the range from narrowing too much so as to permanently exclude useful data outside the expected range. More complex formulae ore even changing the valueof the 2× the expected range could be used but this is the easiest one we found to apply and one which worked well. All reasonable variations within the skill of the ordinary practitioner would be considered within this teaching, so long as they resulted in the points allowed being within some range beyond the expected range. The expected ranges are updated by combining a fraction of the current value of the mean or MAD (given by the variable "A" in FIG. 13, S198, which is preferably 90% or greater), with a small fraction of a new estimate of the mean or MAD (the "(1-A)" term in the equations in S198). This process is equivalent to filtering with a first order infinite impulse response filter. It is similar to an exponential moving average process and variations on it will be apparent to those of ordinary skill.

After the expected ranges of qualified parameters are updated (step S198) the algorithm can move on to the important step of calculating the ischemia parameter. In Step S199 we place on final constraint for candidate cardiac cycles before the data from them can participate in the calculation of the ischemia parameter: The ST change parameter must be within twice its expected range.

To summarize, in order for the sampled data taken from a particular cardiac cycle to be used in calculation of the ischemia parameter, it must: (a) have >4 out of 7 of the parameters within their expected ranges, or have 12 of 12, 13 of 14, 14 of 16 . . . of the most recent cardiac cycles rejected by the 4 out of 7 criteria, and (b) the current cardiac cycle must have its ST change parameter within twice the expected range for the ST change parameter. If both these requirements are met, we go to step 200, otherwise back to step S100.

Figure 14:
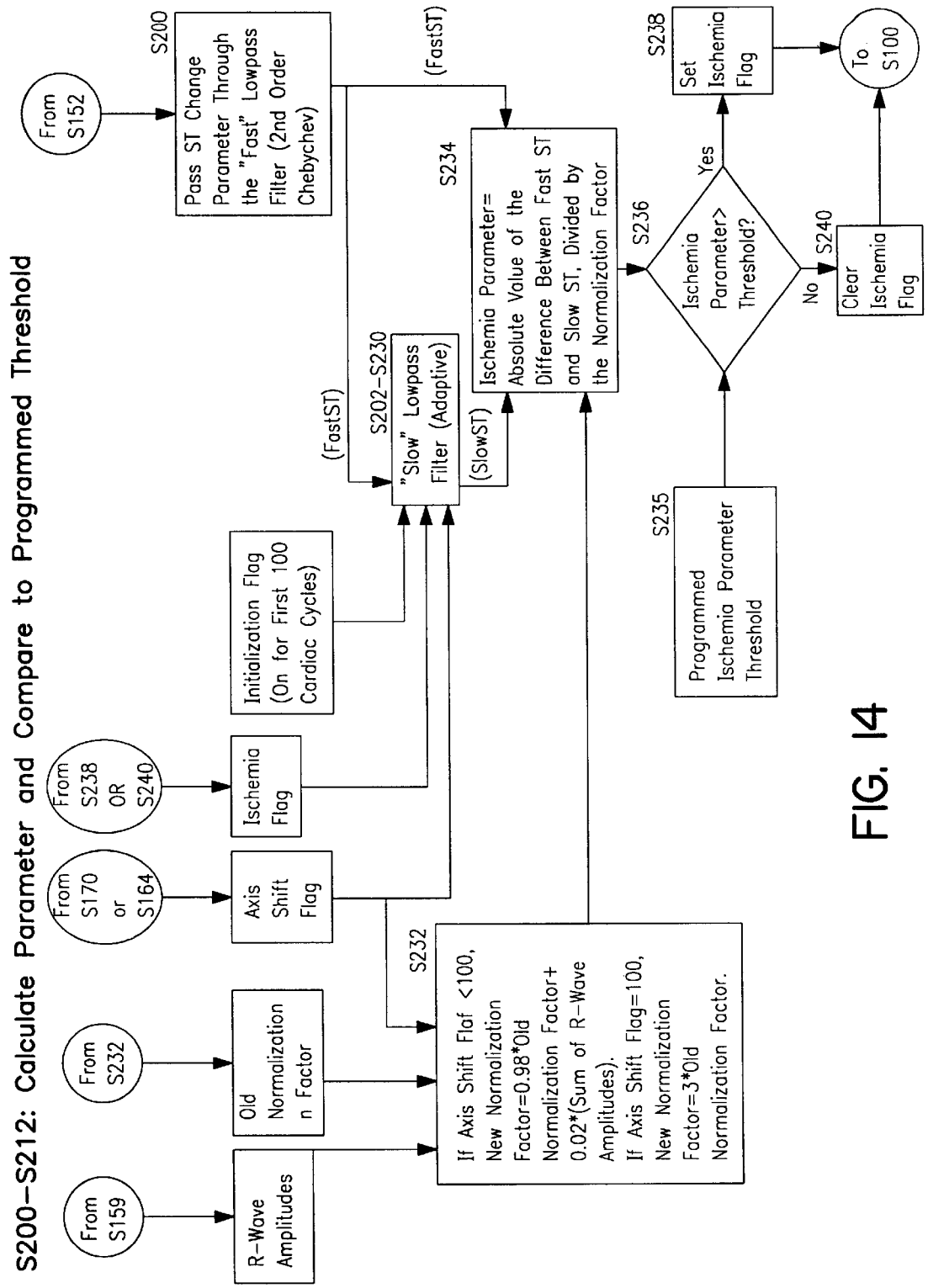
Figure 15:
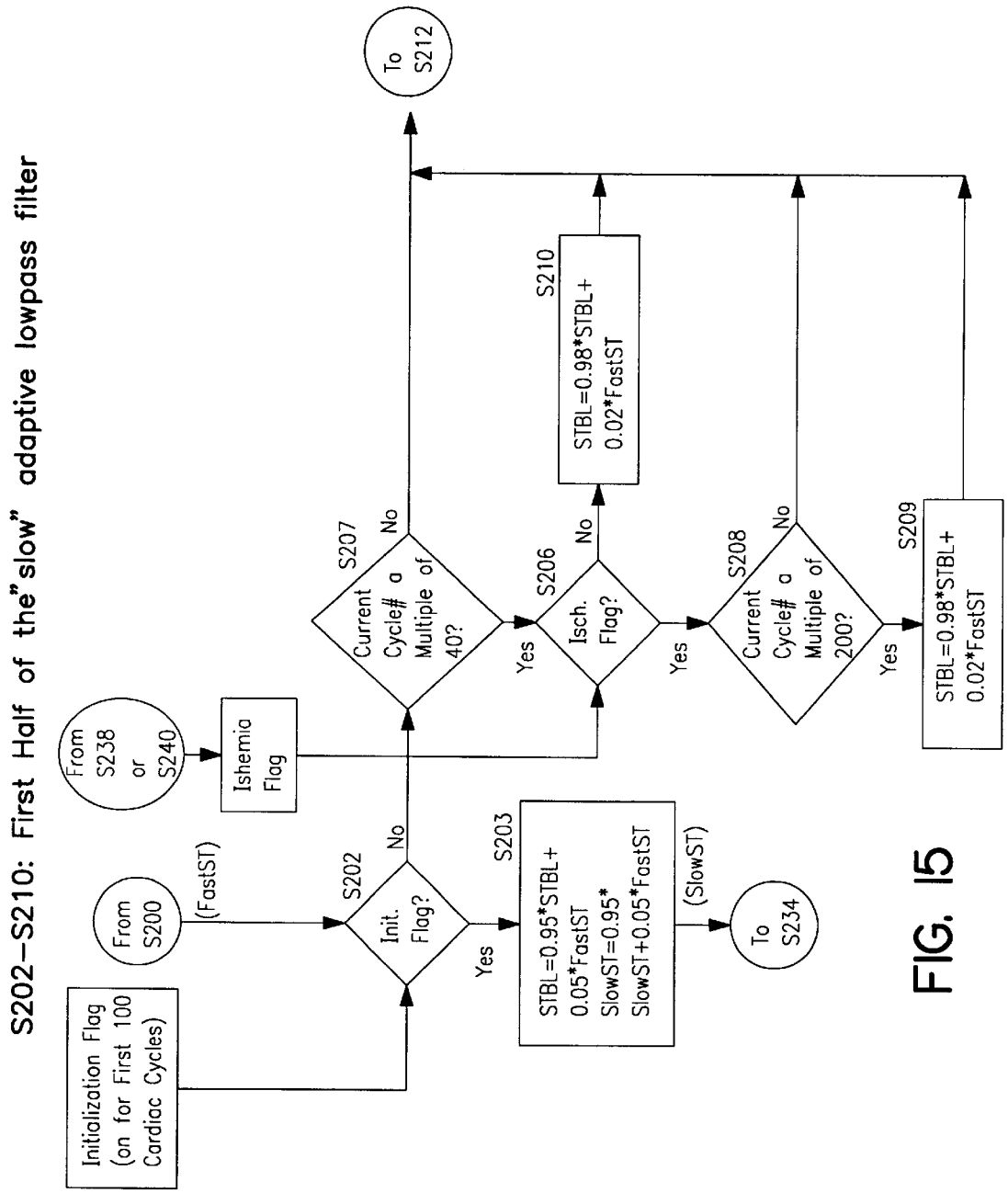
Figure 16:
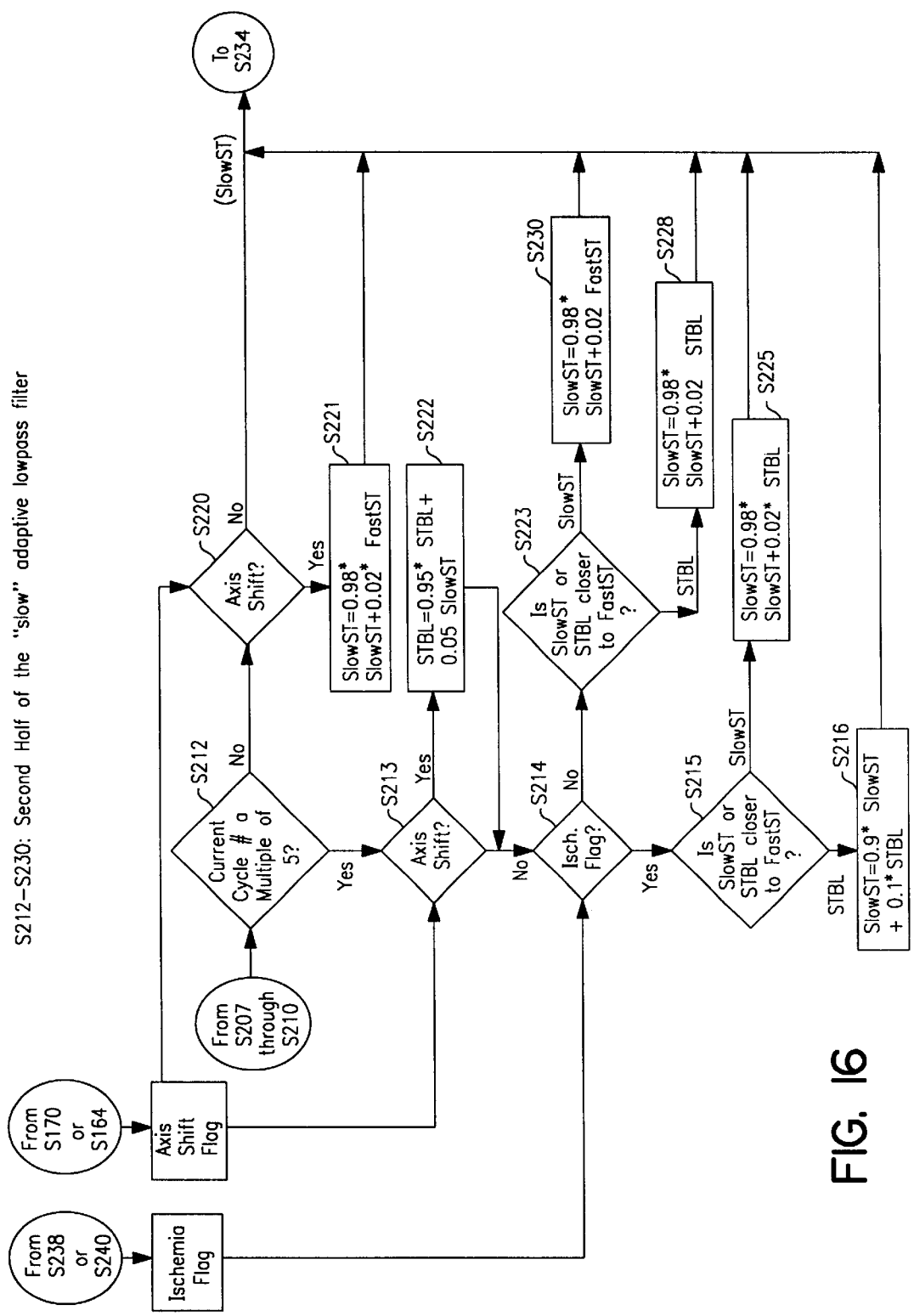

FIGS. 14–16, combined together, are a block diagram of the steps S200–S240 of the final stage of FIG. 6 wherein the ischemia parameter is calculated and compared to the programmed ischemia parameter threshold. The basis of the ischemia parameter is the ST Change parameter (calculated in step S152). For each of the three lead vectors, the ST Change parameter is passed consecutively through a "Fast" lowpass filter in step S200 and the resulting "FastST" signal is then passed through a "Slow" lowpass filter of steps S202–230 (depicted in FIGS. 15 and 16).

The Fast lowpass filter of step S200 is preferably a $2^{nd}$ order Chebychev Type II filter with a cutoff near pi/20 (radians per cardiac cycle) which excludes fluctuations of the ST Change parameters that occur faster than physiologic ST deviation changes. The filter characteristics are tuned from empirical data of human ischemic ST deviation changes. Other filters may be used including for example a Butterworth, or any other filter one of ordinary skill in the digital signal processing art might employ. The important feature is that the filter allow to pass primarily that part of the ST change signal that changes no faster than physiologic changes consistent with human cardiac ischemia.

The Slow lowpass filter is a complex nonlinear adaptive filter set forth in steps S202–S230 which is designed to pass only the baseline drift, i.e., the positive or negative deviations from the baseline caused by drift, as an absolute "SlowST" absolute signal, which we might call an 'ST baseline signal.' The ischemia parameter is then derived as the absolute difference between the FastST and SlowST signals, normalized by a normalization factor proportional to the R-wave amplitude or vector magnitude in step S234. A bandpass filter is effectively created in steps S200, S202–230 and S234 by subtracting the SlowST signal from the FastST signal for each lead vector. This approach is followed in recognition that physiologic ischemic changes in the ST segment fall in a bandpass region, where elevation or depression changes that occur too fast are due to noise or axis shifts and changes that are too slow are caused by medication, electrolyte disturbances, or other forms of baseline drift. The bandpass filter approach is designed to pass only those ST changes that are due to ischemia.

The normalization factor (NF) is obtained in step S232 as a running mean of the sum of three R-wave amplitude parameters(one for each lead vector). Alternatively, the normalization factor could be obtained as a running mean of the vector magnitude of the R-wave vector.

In step S232, the "new NF" is derived in one of two ways, depending on the current count of the axis shift flag counter. As shown in FIG. 12, the axis shift flag count was either set to 100 in step S170 in response to detection of an axis shift or was set to a count less than 100 in step S164 because the axis shift criteria were not met. The "old NF" is abruptly increased by a large amount, we use a factor of three when the axis shift flag count is set to 100, so that a sudden change in the ST change parameter that can result from an axis shift is not misinterpreted as ischemia. The factor of three change is selected because it provides a good indicator of an axis shift but the artisan of ordinary skill could chose to recognize the axis shift in another way.

If the ischemia flag counter is less than 100, the new NF is derived from the formula "new NF=0.98×old NF+0.02× (Sum of all R-wave amplitude parameters). This equation's numbers and form of this equation are chosen to change the factor slowly so that rapid changes in the R-wave amplitude will not cause rapid changes in the ischemia parameter. Similar programmable equations could be used which accomplish the same result within the ordinary skill of the programmer/engineer.

Returning to step S234, each of the three ischemia parameters (IP) for each lead vector (or spatial vector)is determined from the formula:

$$IP = |(FastST - SlowST)/new\ NF|$$

In step S236, each ischemia parameter is compared to an ST ischemia parameter threshold previously programmed into a register in step S235. In preferred embodiments, three ischemia parameters are added and compared to a single threshold. Alternatively, if any one ischemia parameter exceeds its ischemia parameter threshold, ischemia is declared by setting an ischemia flag in step S238. Ischemia is not declared and the ischemia flag is cleared in step S240 if none of the ischemia parameters exceed the ischemia parameter threshold. The setting of the ischemia flag is employed to trigger delivery of a therapy and/or storage of EGM and any sensor data, and the algorithm returns to the standby stage S100 of FIG. 6.

FIGS. 15 and 16 describe in detail the operation of the nonlinear, adaptive "SlowST" filter in steps S202–S230. The purpose of this filter is to update the "SlowST" parameter, by slowly tracking either the "FastST" parameter or an internal parameter called "STBL", which is an estimate of the very slowly moving baseline of the ST Change parameter. The method by which SlowST is updated depends on the status of the ischemia flag, the axis shift flag count, an initialization flag (which preferably is active for the first 100 cardiac cycles of operation), and the current values of SlowST, FastST, and STBL. To decrease the rate of change of the SlowST parameter, it is typically updated only on every fifth cardiac cycle (step S212), whereas the STBL parameter is only updated every fortieth cardiac cycle (step S207). The SlowST parameter is updated rapidly when the initialization flag is set (step 203), less rapidly when there is an axis shift (step S221), and very slowly otherwise (steps S216, S225, S228, and S230).

Thus, in FIG. 15, the status of the initialization flag is first checked in step S202, and if it is set, the values of STBL and SlowST are recalculated in step S203.

We would adapt this system for devices having any kind of leads and providing any kind of therapy. For example, refer to FIG. 1 in which the heart 10 pumps oxygenated blood out through the aortic arch 12, which leads to the right subclavian artery 14, the right common carotid 16, the left common carotid 18, the left subclavian artery 20, and the thoracic aorta 22. Stretch receptors located in the arterial walls in the aortic arch 12 and at the bifurcation of the carotid arteries in the carotid sinus portion of the neck may be stimulated by electrical pulses, as may other cardiac system affecting nerve sites, to reduce the effects of and possibly eliminate the danger of an ischemic situation found by our system.

For example, the rate of the heart 10 can be restrained by the right and left vagus nerves, and cardiac depressor nerves. The cardio-inhibitory center of the nervous system exerts a tonic effect upon the heart, via the vagus nerves, acting through what is called vagal tone. With vagal stimulation, it is possible to slow the heart rate down and allow more complete cardiac relaxation, which may lead to less of a deleterious effect upon the cardiac tissue caused by an ischemic condition. Accordingly knowing something about an ischemic condition allows one to provide assistance to the heart through affecting vagal tone, or through taking various other measures. It might use for example a device as described in U.S. Pat. No. 5,752,976 to warn a health care provider of the situation, while perhaps stimulating the nerves directly using the system of U.S. Pat. No. 5,199,428 (both incorporated by this reference in their respective entireties).

Also, introduction of various medicaments can have similar effects on vagal tone, and other biologically active agents can be used to directly treat the condition of ischemia. To do so the teachings of for examples, U.S. Pat. Nos. 5,458,631, and 5,551,849 may be used. Further, communication from one device sensing an ischemic condition can communicate with other devices for providing therapy using the teachings of, for one example, U.S. Pat. No. 4,987,897, The Funke Body Bus. Accordingly, the teachings of this disclosure make it possible to know that ischemia is present and thus allow for the opportunity to treat it.

Use of Multidimensional versus Multiple Single-dimensional "expected ranges"

By comparing each parameter from each vector to its own independent expected range, the inter-dependencies of parameters is not taken into account and the form of the expected range is highly constrained. For example, comparing the two R-wave slope parameters obtained from two lead vectors to two separate one-dimensional expected ranges produces two results: First R-wave slope inside or outside of its expected range and second R-wave slope inside or outside of its expected range. If the two R-wave slopes are plotted on a two dimensional graph, with the first R-wave slope plotted on the abscissa and the second R-wave slope plotted on the ordinate, the two independent expected ranges form an "expected rectangle". The advantage of this type of comparison is that one result is obtained, whether or not the R-wave slopes are inside or outside of the expected rectangle. By carrying this analogy one step further, the expected range of 2 R-wave slopes (taken for two electrode vectors for example) can be defined as a circle in two-dimensional space. In this situation, rather than asking if each of the two R-wave slopes lies within each of the two expected ranges (each defined by two parameters, the mean and MAD), we are asking if a mathematical combination of the two R-wave slopes falls within an expected space that is defined by only 3 parameters: the center and radius of the circle. Since a multidimensional expected range can take on any shape, we can include inter-dependencies of parameters. For example, we may find that it is acceptable for one parameter to take on a small value only if a second parameter has a large value. This sort of inter-dependency is easy to implement with a multidimensional expected range. Accordingly we only require a few additional computational steps to define the range space in whatever shape is preferred, and the currently determined values for the particular parameter are checked by the same computation to see if they are within the range shape. This is preferably done for each of the parameters, and changes to the expected ranges are only made when parameters fall within twice the expected range.

Use During Cardiac Pacing

Finally, it should be noted that these processes can be applied during cardiac pacing even though the waveform in the paced electrogram is not typically useful for such systems as we have invented due to the morphology of the waveform generally having a rapid change in the ST segment as a normal part of the profile. We simply either raise the pacing rate to a fixed level for a small number of at least three beats per minute and use only the data from that three beat set, thus assuring ourselves of near exact localization of the sample data points relative to each other across the three cycles. Alternatively we could lower the rate to allow the intrinsic beat rate to appear and after a short run use those beats' data. As a third alternative, the fiducial point (which was previously defined as the peak of the R-wave) could be defined as the precise time that the pacing stimulus is applied for a paced beat. In other words, simply adopting a fixed point in the pacing pulse can be used to replace the hunt algorithm and mechanism for finding the R-wave peak as the fiducial point. The timing of the ST measurements would then be fixed relative to the pacing stimulus to ensure that the ST measurements are conducted consistently in the complex morphology of a paced electrogram.

Other Illustrations

Figure 17:
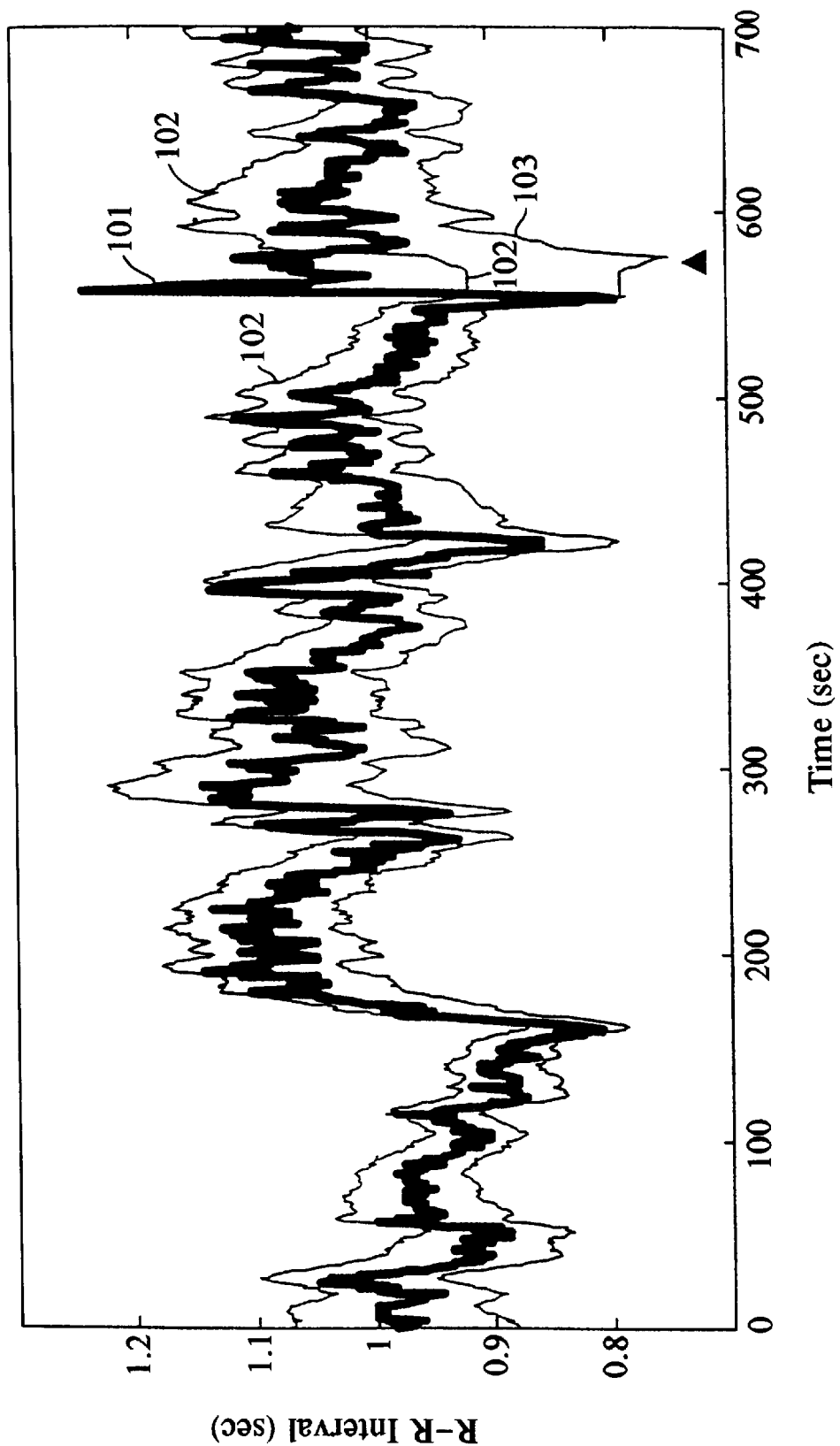
FIGS. 17–19 are graphs.

In FIG. 17, the R—R interval (thick line) is followed and compared to its expected range (mean+/−3*MAD) identified by the thin lines on this graph of interval size in seconds vs. time. At about 550 seconds, the R—R interval line 101 passes well outside the upper line 102 of the expected range for an extended duration. The expected range remains steady for 12 cardiac cycles, waiting of the noise to end. However, the process described above determines that a new normal has developed and adapts (at the point of the upward arrowhead, towards 580 seconds), moving up both lines 102 and 103 to accept the new normal variation.

Figure 18:
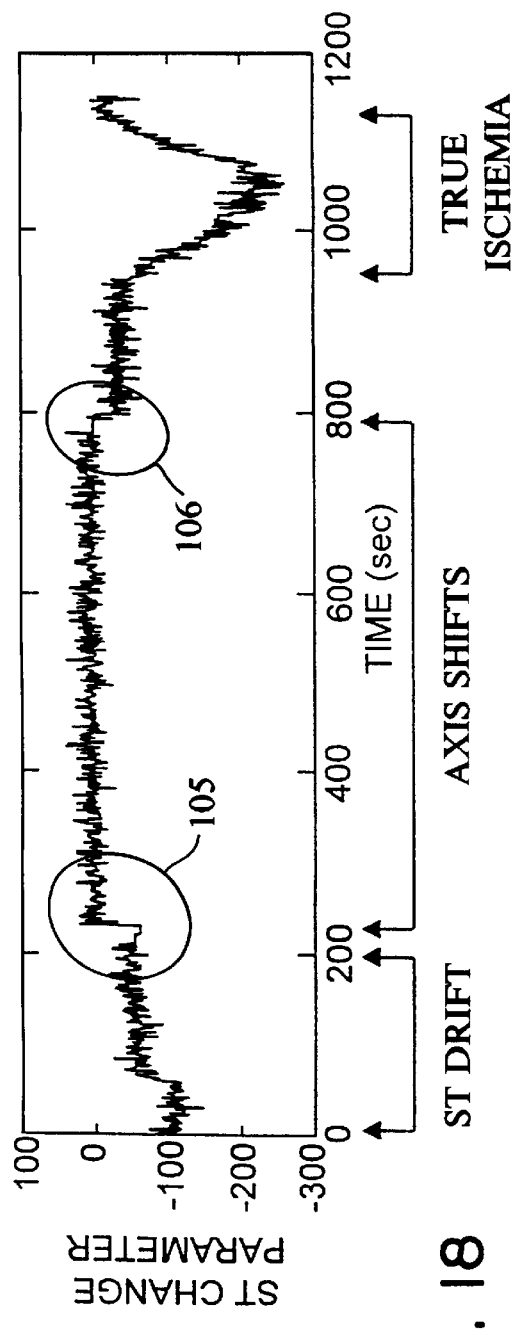

FIG. 18 illustrates a moving ST change parameter, showing two situations which will be filtered out, the ST drift, and the axis shift situations, and the one case in which the rate of change of hte ST change parameter is consistent with human myocardial ischemia, thus giving the device a trigger to report an ischemic condition, commit to a therapy option or otherwise provide a useful response or data record. Notice that drift can cause a substantial change in the ST change parameter but because the rate of change is slow, the drift is excluded from the ischemia parameter result. Similarly, axis shifts can cause a significant change in the ST change parameter, but because of the rapid rate of change, the axis shift is excluded from the ischemia parameter result. Two axis shifts are shown at 105 and 106.

Figure 19:
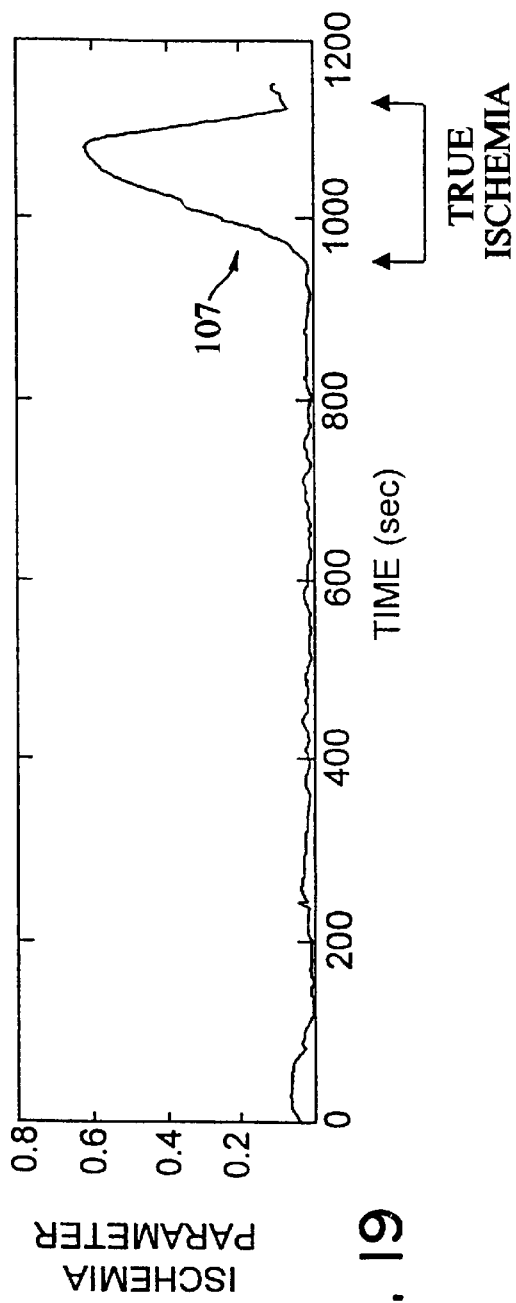

In FIG. 19, the ischemia parameter that results from the ST change parameter run thorough the processes described above is shown. Note that only the physiologically identifiable change registers as a high probability ischemic event at 107.

In FIG. 20 area 201 is that formed by the independent expected ranges of two parameters, let us say, R-wave amplitude parameters for two vectors, for example. Compare this to a 2-D parameter value "allowed ellipse" 202, formed by a combination of the parameter values by some preferred limit function. Thus, comparing 2 separate parameters to 2 separate 1-D allowed ranges is comparable to comparing a 2-D parameter value to an "allowed rectangle" as opposed to the ellipse defined by the limiting function and the ranges of the two parameters. This could expand the allowed space to beyond the rectangle by, for one example, drawing a circle around the outside of the rectangle, thus providing some flexibility in using this concept. If a shape surrounding the rectangle provides enough assurance that both parameters are OK, one could use such a function, whereas if any change in the parameter is considered risky, the function inscribing a smaller shape within the rectangle would be preferred.

It will be apparent to those skilled in the art that the electronics of the system described above are easily attainable using available technology. The electronics may be embodied in custom integrated circuit and software based microprocessor technology and certain of the steps of the algorithm could be reduced to hardware.

It will thus be appreciated that the present invention as described above defines a system having distinct advantages over previously existing systems for detecting ischemia. This system features a high degree of specificity to ischemic conditions and a high degree of flexibility for recognizing and, in therapy delivery configurations, treating ischemic conditions and/or arrhythmias of the heart frequently associated with coronary artery disease and myocardial insufficiency.

It should be noted that additional information regarding ischemia can be had from different sensors. For example, using an accelerometer implanted in the apex of the heart using a lead mounted sensor similar to what is described in US Pat. No. 5,480,412 issued to Mouchawar, et al, (incorporated by reference herein in its entirety by this reference), L. Padeloetti, et al in an abstractissued in the 20th Anniversary of Cardiostim (17-3) has found that the peak endocardial acceleration signal changes correlate well with episodes of coronary artery occlusion. Similarly, pressure sensors as are known for example, from U.S. Pat. No. 5,535,752 (also incorporated by reference in its entirety by this reference) in the heart could sense the pressure variation resulting from an ischemic condition. (See also U.S. Pat. No. 5,025,786 issued to Siegel, also incorporated by this reference, for pressure sensing for ischemia). Thus, with a corresponding signal from such a sensor (which could have an electrodes mounted on it for sensing electrical activity also within the heart to produce another set of electrocardiogram vectors as well), a redundancy signal can be established based on the pressure or acceleration signal that will confirm, in an additional step in the algorithm, that following an axis shift, keeping data, excluding data and so forth is or is not appropriate. If, for example, such an accelerometer or pressure sensor reports decreases in the accelerometer or pressure signal which is tending to indicate that an ischemic condition might be occurring at the same time there is an ST change parameter indication of the same condition, then there is a mechanical verification (pressure, acceleration) of the electrically detected (S-T change parameter) event, and the specificity of the ischemia detection can be increased. Therefore, the most aggressive device therapy, patient alert, or diagnostic option may be initiated when both parameters concur. If on the other hand, the new sensor signal (Acceleration/pressure) does not show signals that correspond well to ischemia, the algorithm could provide that a greater ST parameter change is required to trigger diagnostic data collection, patient alert, or therapy.

Further, since many electrical axis shifts in the ECG may be due to postural changes, the use of an accelerometers as have been previously taught can detect postural changes. Therefore, the accelerometer can be used as a redundant signal to verify that a particular axis shift which is detected on the ECG corresponded with a change in the patient posture.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications and alterations should therefore be seen within the scope of the present invention.

What is claimed is:

1. A method for determining whether there has been an axis shift in an electrocardiogram waveform comprising a repeated cycle of steps, each cycle comprising the steps:
    a) for a given cardiac cycle, collecting into a buffer selected characteristic portions of the electrocardiogram signal including a fiducial point within said electrocardiogram signal;
    b) determining a selection of samples surrounding temporally said fiducial point, and based on values of electrocardiogram amplitude of said samples producing a parameter representative of said a cardiac cycle;
    c) determining if said parameter is out of an allowable range of said parameter, wherein the size of said range is adaptively determined based on previously-calculated values for said parameter; and
    d) declaring an axis shift if said parameter is out of said range for more than a predetermined amount of time.

2. The method of claim 1 wherein said predetermined amount in step d comprises a predetermined number of times out of a predetermined number of cycles.

3. The method of claim 1 wherein said fiducial point is an R-peak for said a cardiac cycle, and the following steps are used to determine the R-peak point;
    finding a peak positive value and a peak negative value in said buffer of samples,
    finding an isoelectric sample,
    employing the amplitude value of said isoelectric sample and said peak values to determine which of said peak values is furthest from said isoelectric sample value,
    declaring the sample with the peak value further from said isoelectric sample value as the sample located at said R-wave peak.

4. The method of claim 3 wherein in step "b" said parameter value is an amplitude of an R-wave and is determined based on said R-wave peak value.

5. The method as set forth in claim 1 wherein said declaration of said parameter axis shift is used to determine ranges for acceptable values for determining a physiologic characteristic from the set of physiologic characteristics including T wave height variation, ischemic condition or QT variation.

6. The method of any of claims 1–3 further comprising the step of simultaneously performing steps a–d on a plurality of electrocardiogram vectors, and still further comprising the step of determining an axis shift combination value based on whether an axis shift is declared for more than a predetermined number of electrocardiogram vectors.

7. The method of any of claims 1–5 and further comprising the step of adjusting an alarm threshold for a physiologic parameter change based on whether an axis shift is declared.

8. The method of any of claims 1–5 further comprising the step of adapting baseline values of said measured parameter to change responsive to declaration of an axis shift.

9. The method of any of claims 1–5 further comprising the step of adapting ST change variable filter coeficients responsive to declaration of an axis shift.

10. The method of any of claims 1–5 further comprising the step of adapting a noise filter to reduce sensitivity to motion artifacts in a group of cardiac cycles surrounding the temporal location of a declaration of an axis shift.

11. A method for determining whether an axis shift has occurred in an electrocardiogram (EGM) waveform, comprising the methods of:
    a) obtaining samples of the EGM waveform over a predetermined number of cardiac cycles;
    b) calculating a predetermined parameter indicative of a selected characteristic of the EGM waveform;
    c) repeating steps a) and b), and updating the predetermined parameter based on newly-obtained samples of the EGM waveform and on previously-calculated values of the predetermined parameter;
    d) determining an allowable range of values for the predetermined parameter, the size of the allowable range being based on a current value and at least one previous value of the predetermined parameter as calculated in method c); and
    e) determining that an axis shift has occurred if the predetermined parameter is outside the allowable range of values for a predetermined period of time.

12. The method of claim 11, wherein method e) includes the method of determining that an axis shift has occurred if the predetermined parameter is outside the allowable range of values for a predetermined number of cardiac cycles.

13. The method of claim 11, wherein method a) obtains samples of the EGM waveform for one or more characteristic portions of the predetermined number of cardiac cycles.

14. The method of claim 13, wherein the one or more characteristic portions include a fiducial point of a cardiac cycle, and wherein method a) includes the methods of:

determining an isoelectric signal level for the EGM waveform; and selecting the fiducial point of the cardiac cycle as the point of the cardiac cycle wherein the signal amplitude deviates the most from the isoelectric signal level.

15. The method of claim 11, wherein the selected characteristic is the amplitude of an R-wave of the EGM waveform.

16. The method of claim 15, wherein method c) includes the method of obtaining a running mean value of the amplitude of the R-waves for multiple cardiac cycles.

17. The method of claim 11, and including the methods of:

performing methods a) through d) for multiple vectors of the EGM waveform; and wherein method e) includes the method of determining that an axis shift has occurred if the predetermined parameter is outside the allowable range of values for a predetermined period of time for a predetermined number of the multiple vectors.

18. The method of claim 11, and further including the methods of:

calculating one or more parameters from the EGM waveform to be used to evaluate a physiological condition; and evaluating the physiological condition using acceptable ranges for each of the one or more parameters, wherein the acceptable ranges are determined based on the axis shift determination from method e).

* * * * *